United States Patent [19]
DeFonzo et al.

[11] Patent Number: 5,560,532
[45] Date of Patent: Oct. 1, 1996

[54] APPARATUS AND METHOD FOR APPLYING SURGICAL STAPLES TO BODY TISSUE

[75] Inventors: Stephan A. DeFonzo, Bridgeport; Samson L. Pennatto, Danbury; Andrew Komlosi, Fairfield, all of Conn.

[73] Assignee: United States Surgical Corporation, Norwalk, Conn.

[21] Appl. No.: 134,402

[22] Filed: Oct. 8, 1993

[51] Int. Cl.⁶ .................................................. A61B 17/068
[52] U.S. Cl. ........................ 227/176.1; 227/19; 227/175.1
[58] Field of Search ............................. 227/19, 175, 176, 227/177, 178, 180, 181, 175.1, 176.1

[56] References Cited

U.S. PATENT DOCUMENTS

| | | |
|---|---|---|
| Re. 28,932 | 8/1976 | Noiles et al. . |
| Re. 33,362 | 10/1990 | Mongeon et al. . |
| 3,054,406 | 9/1962 | Usher . |
| 3,124,136 | 3/1964 | Usher . |
| 3,494,533 | 2/1970 | Green et al. . |
| 3,593,903 | 7/1971 | Astafiev et al. . |
| 3,643,851 | 2/1972 | Green et al. . |
| 3,837,555 | 9/1974 | Green . |
| 3,955,581 | 5/1976 | Spasiano et al. . |
| 4,014,492 | 3/1977 | Rothfuss . |
| 4,043,504 | 8/1977 | Hueil et al. . |
| 4,127,227 | 11/1978 | Green . |
| 4,196,836 | 4/1980 | Becht . |
| 4,204,623 | 5/1980 | Green . |
| 4,207,873 | 6/1980 | Kruy . |
| 4,256,251 | 3/1981 | Moshofsky . |
| 4,261,244 | 4/1981 | Becht et al. . |
| 4,317,535 | 3/1982 | Huftel et al. . |
| 4,321,002 | 3/1982 | Froehlich . |

(List continued on next page.)

FOREIGN PATENT DOCUMENTS

| | | | |
|---|---|---|---|
| 0041022 | 12/1981 | European Pat. Off. . | |
| 0593920 | 4/1994 | European Pat. Off. ................ | 227/175 |

OTHER PUBLICATIONS

M-D-D-I Report, Sept. 1991 Ethicon Endoscopic Staple for Hernia Repair.

Publication Entitled Shape Memory Alloys From Scientific American Nov. 1979.

Publication Entitled "A Quick Stapler Tie-Over Fixation For Skin Grafts", by Haim Y. Kaplan, M.D., Ann. Plast. Surg., 22:173, 1989, pp. 173–174.

Publication Entitled "A Rapid and Effective Method of Skin Graft Stabilization in Burned Children", by J. B. Boyd et al., The Hospital For Sick Children, Toronto, Canada, 1982, pp. 400–401.

Publication Entitled "A Simple Bolster Technique For Skin Grafting", by Henry T. Hoffman, M.D. and Michael LaRouere, M.D., Department of Otolaryngology, University of Michigan, Laryngoscope 99, May 1989, pp. 558–559.

Information Booklet for Auto Suture® Skin & FASCIA Surgical Stapling Instruments and Disposable Loading Units, ©1978 United States Surgical Corporation.

Information Booklet for Auto Suture® MULTIFIRE PREMIUM™ Disposable Skin Stapler and Disposable Loading Unit, ©1981, 1990, United States Surgical Corporation.

*Primary Examiner*—Rinaldi I. Rada
*Assistant Examiner*—Allan Schrock

[57] ABSTRACT

Apparatus is disclosed for applying at least one surgical fastener to body tissue, having a frame and a tubular member connected to the frame and extending distally therefrom. The tubular member has a generally longitudinal axis, a proximal end portion, and a distal end portion. At least one surgical fastener is supported by the tubular member, and a mechanism is provided for advancing the at least one surgical fastener distally for positioning adjacent the body tissue. An articulating structure is included for pivotally rotating the distal end portion to predetermined angles with respect to the generally longitudinal axis, where the articulating structure includes a rotatable mechanism rotatable about an axis generally transverse to the longitudinal axis.

30 Claims, 12 Drawing Sheets

U.S. PATENT DOCUMENTS

| | | |
|---|---|---|
| 4,347,847 | 9/1982 | Usher . |
| 4,349,028 | 9/1982 | Green . |
| 4,375,866 | 3/1983 | Giersch et al. . |
| 4,403,693 | 9/1983 | Froehlich . |
| 4,406,392 | 9/1983 | Campbell et al. . |
| 4,407,286 | 10/1983 | Noiles et al. . |
| 4,452,245 | 6/1984 | Usher . |
| 4,470,532 | 9/1984 | Froehlich . |
| 4,489,875 | 12/1984 | Crawford et al. . |
| 4,496,090 | 1/1985 | Crevier et al. . |
| 4,505,273 | 3/1985 | Braun et al. . |
| 4,506,819 | 3/1985 | Rand . |
| 4,519,532 | 5/1985 | Foslien . |
| 4,523,695 | 6/1985 | Braun et al. . |
| 4,523,707 | 6/1985 | Blake, III et al. . |
| 4,526,174 | 7/1985 | Froehlich . |
| 4,527,726 | 7/1985 | Assell et al. . |
| 4,550,715 | 11/1985 | Santangelo et al. . |
| 4,566,620 | 1/1986 | Green et al. . |
| 4,573,622 | 3/1986 | Green et al. . |
| 4,583,670 | 4/1986 | Alvarado . |
| 4,591,086 | 5/1986 | Campbell et al. . |
| 4,592,498 | 6/1986 | Braun et al. . |
| 4,607,638 | 8/1986 | Crainich . |
| 4,610,383 | 9/1986 | Rothfuss et al. . |
| 4,618,086 | 10/1986 | Li et al. . |
| 4,619,391 | 10/1986 | Sharkany et al. . |
| 4,634,035 | 1/1987 | Li et al. . |
| 4,655,221 | 4/1987 | Devereux . |
| 4,662,555 | 5/1987 | Thornton . |
| 4,664,305 | 5/1987 | Blake, III et al. . |
| 4,665,906 | 5/1987 | Jervis . |
| 4,671,279 | 6/1987 | Hill . |
| 4,691,853 | 9/1987 | Storace . |
| 4,719,917 | 1/1988 | Barrows et al. . |
| 4,728,020 | 3/1988 | Green et al. . |
| 4,747,531 | 5/1988 | Brinkerhoff et al. . |
| 4,787,387 | 11/1988 | Burbank, III et al. . |
| 4,789,090 | 12/1988 | Blake, III . |
| 4,802,478 | 2/1989 | Powell . |
| 4,807,628 | 2/1989 | Peters et al. . |
| 4,811,886 | 3/1989 | Murray . |
| 4,821,942 | 4/1989 | Richards et al. . |
| 4,838,884 | 6/1989 | Dumican et al. . |
| 4,874,122 | 10/1989 | Froelich et al. . |
| 4,880,015 | 11/1989 | Nierman . |
| 4,919,152 | 4/1990 | Ger . |
| 4,919,320 | 4/1990 | Storace . |
| 4,944,443 | 7/1990 | Oddsen et al. . |
| 4,951,861 | 8/1990 | Schulze et al. . |
| 5,002,551 | 3/1991 | Linsky et al. . |
| 5,042,707 | 8/1991 | Taheri . |
| 5,049,152 | 9/1991 | Simon et al. . |
| 5,125,553 | 6/1992 | Oddsen et al. . |
| 5,161,725 | 11/1992 | Murray et al. . |
| 5,174,487 | 12/1992 | Rothfuss et al. . |
| 5,222,975 | 6/1993 | Crainich . |
| 5,240,163 | 8/1993 | Stein et al. . |
| 5,246,156 | 9/1993 | Rothfuss et al. . |
| 5,246,450 | 9/1993 | Thornton et al. . |
| 5,251,801 | 10/1993 | Ruckdeschel et al. . |
| 5,289,963 | 3/1994 | McGarry et al. ............... 227/177 X |
| 5,312,023 | 5/1994 | Green et al. ............... 227/19 X |
| 5,326,013 | 7/1994 | Green et al. ............... 227/19 X |
| 5,356,064 | 10/1994 | Green et al. ............... 227/19 X |
| 5,381,943 | 1/1995 | Allen et al. ............... 227/177 |

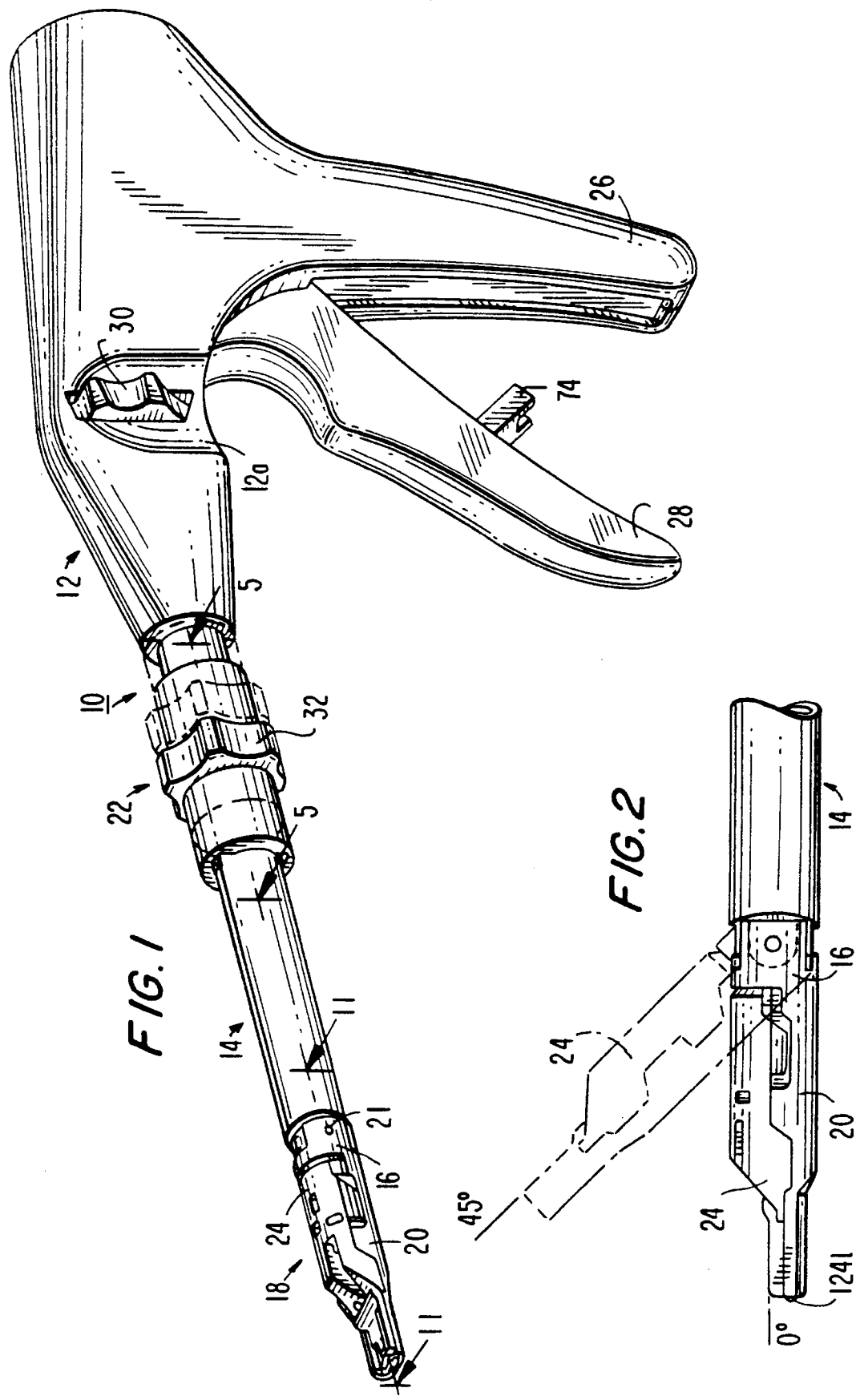

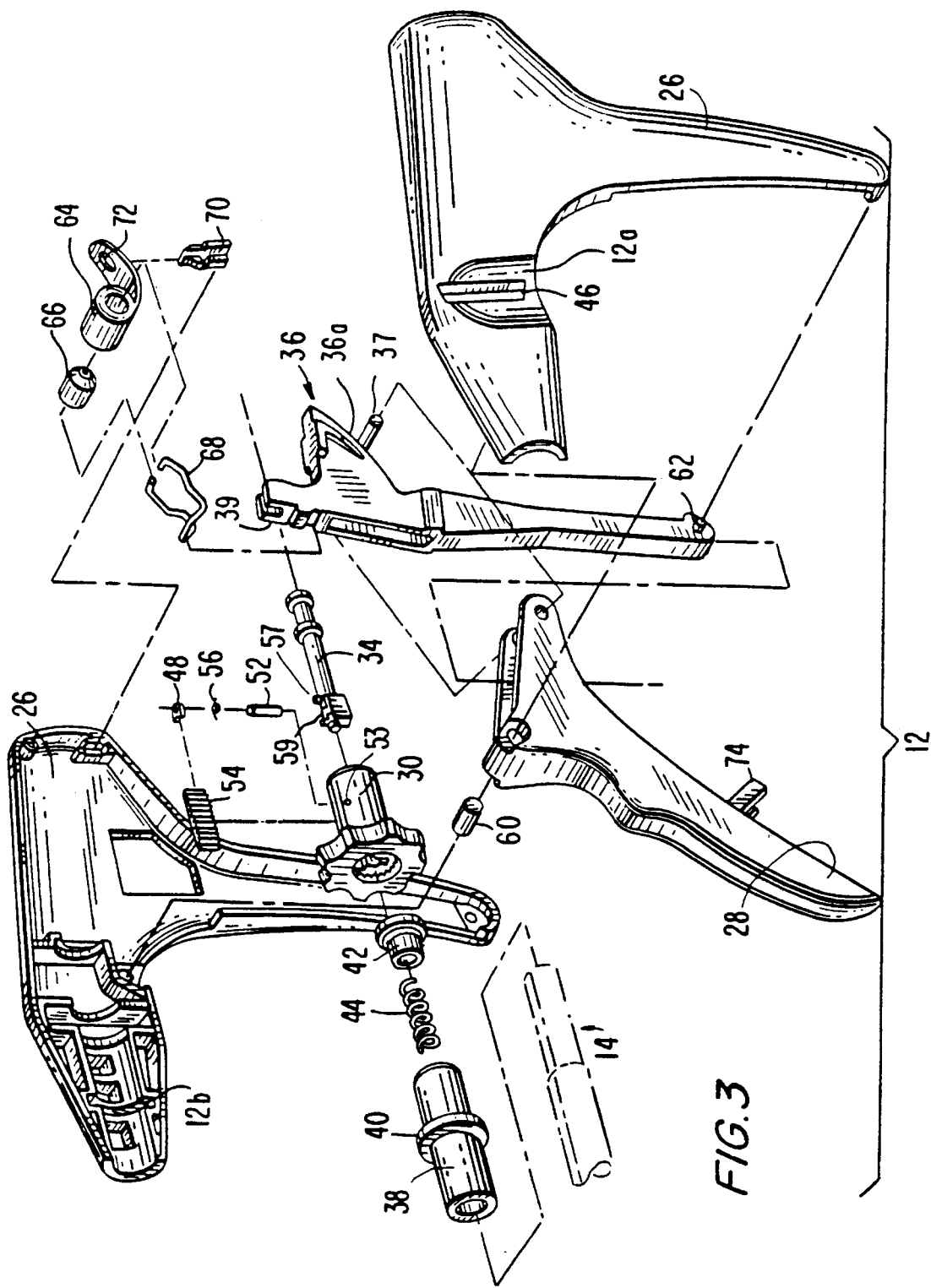

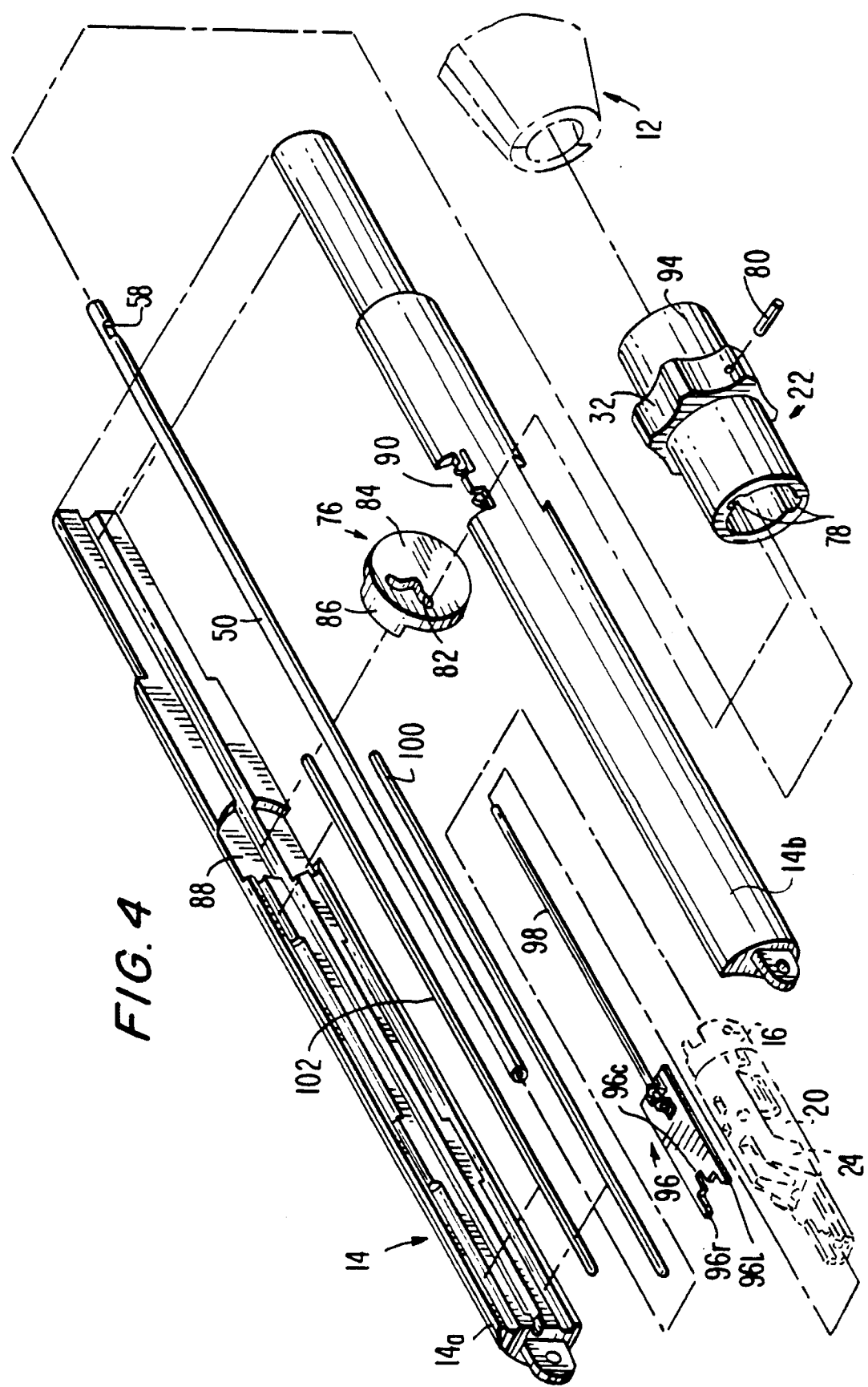

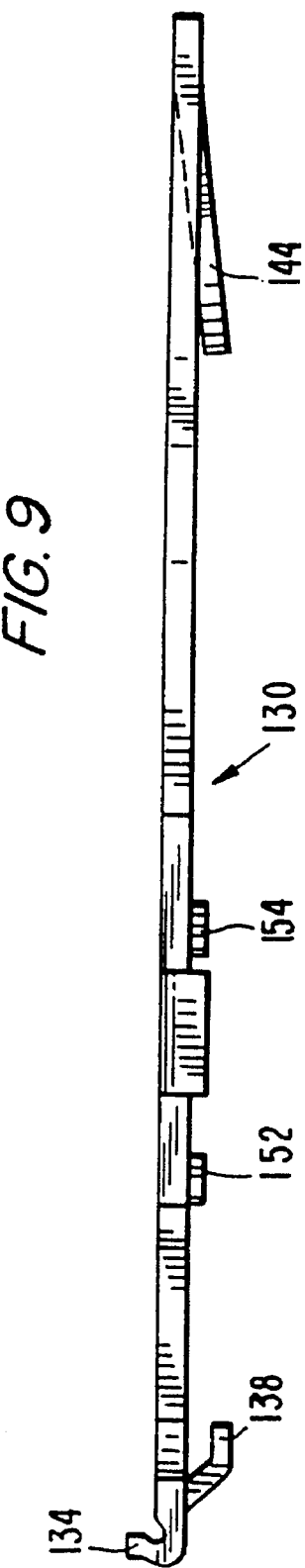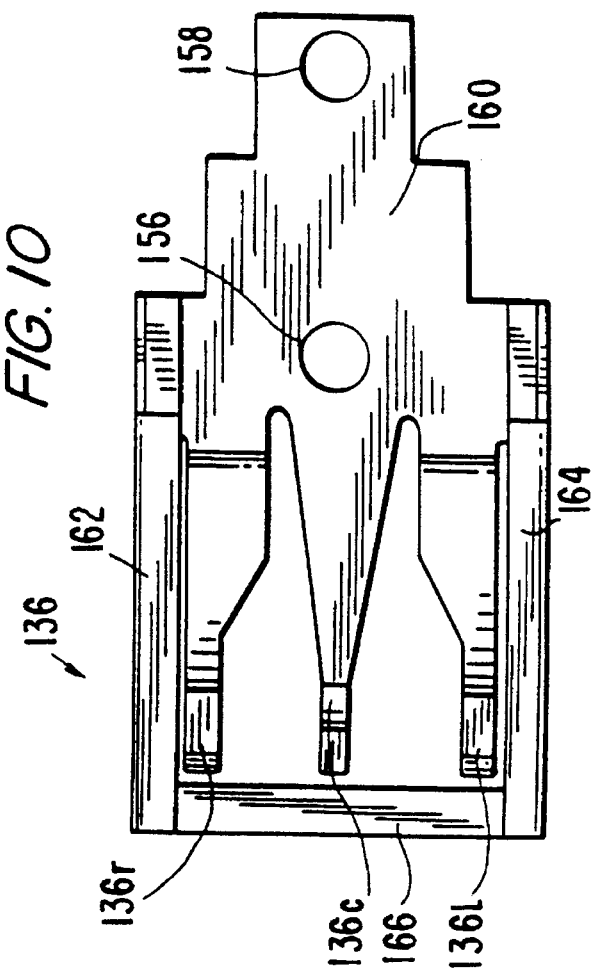

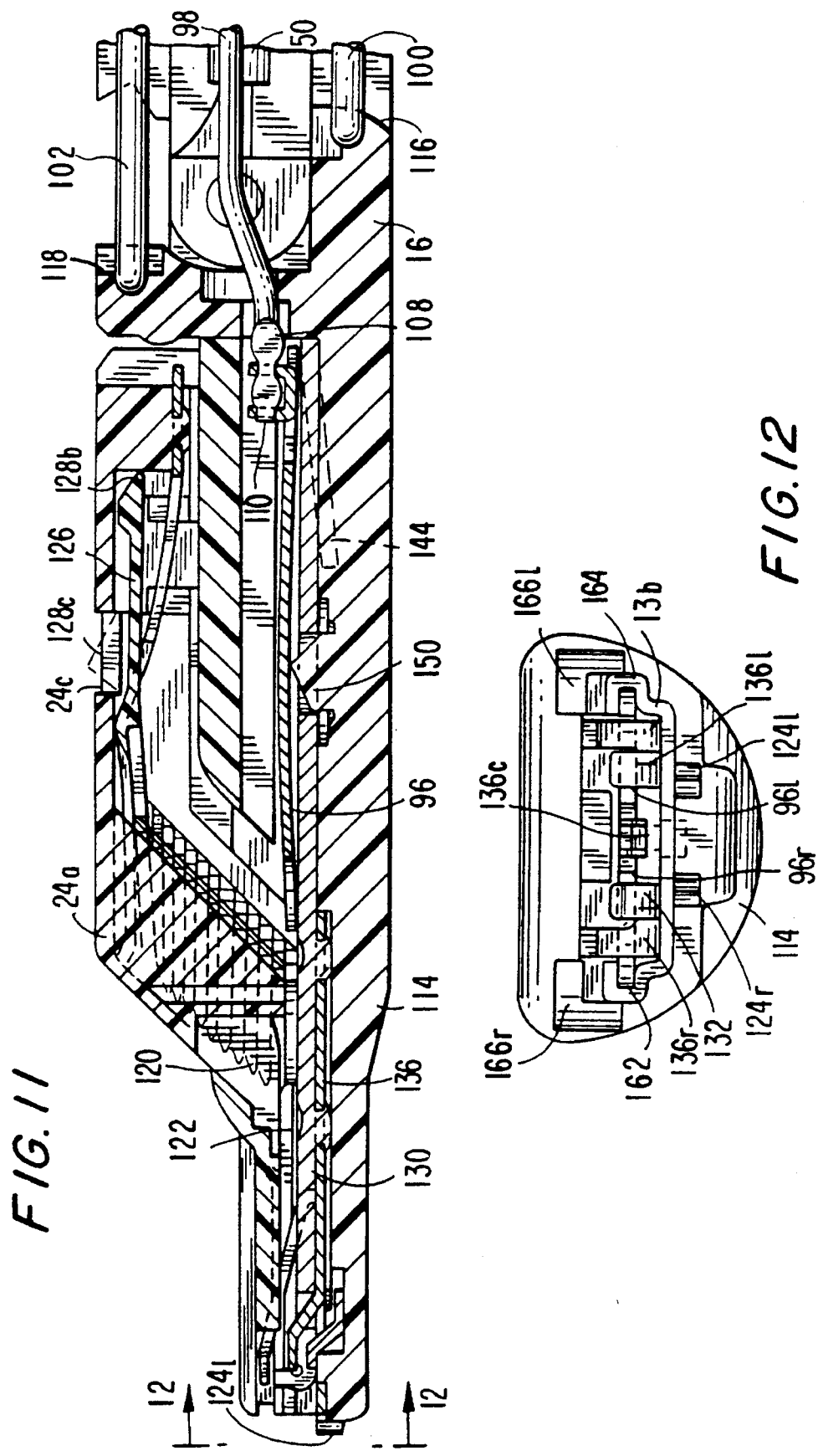

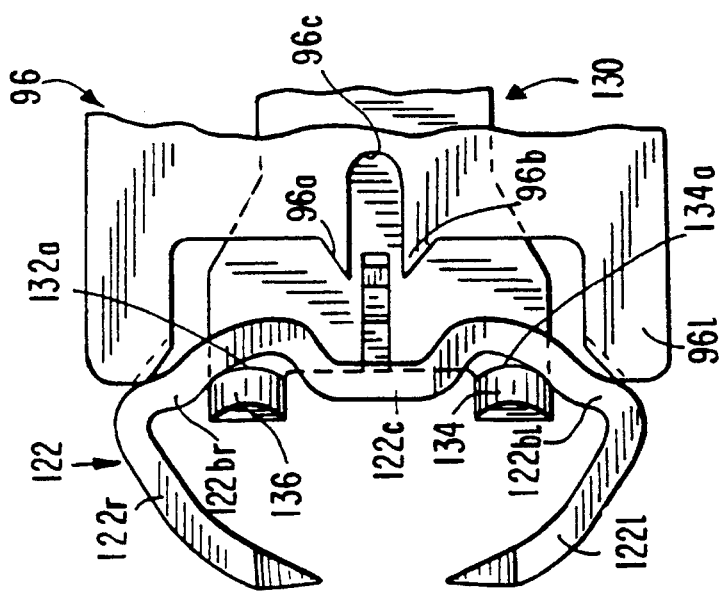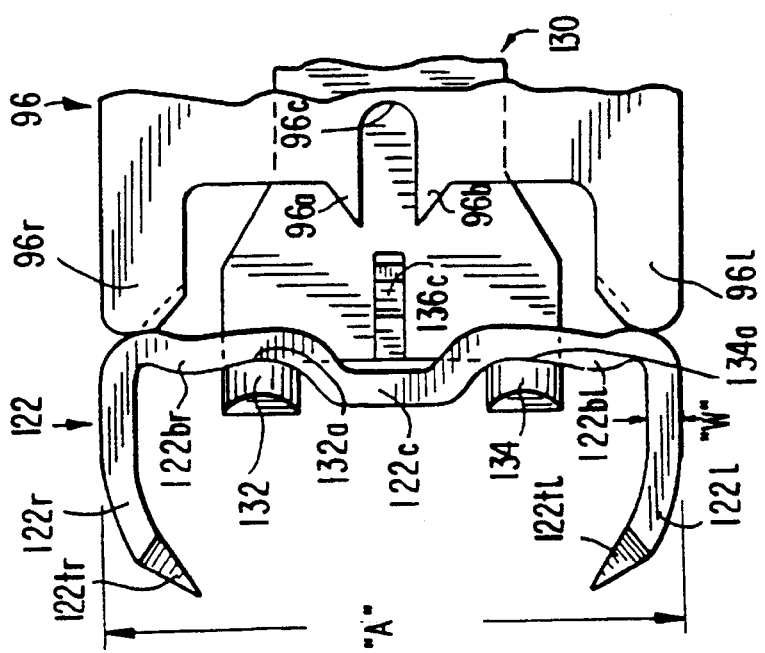

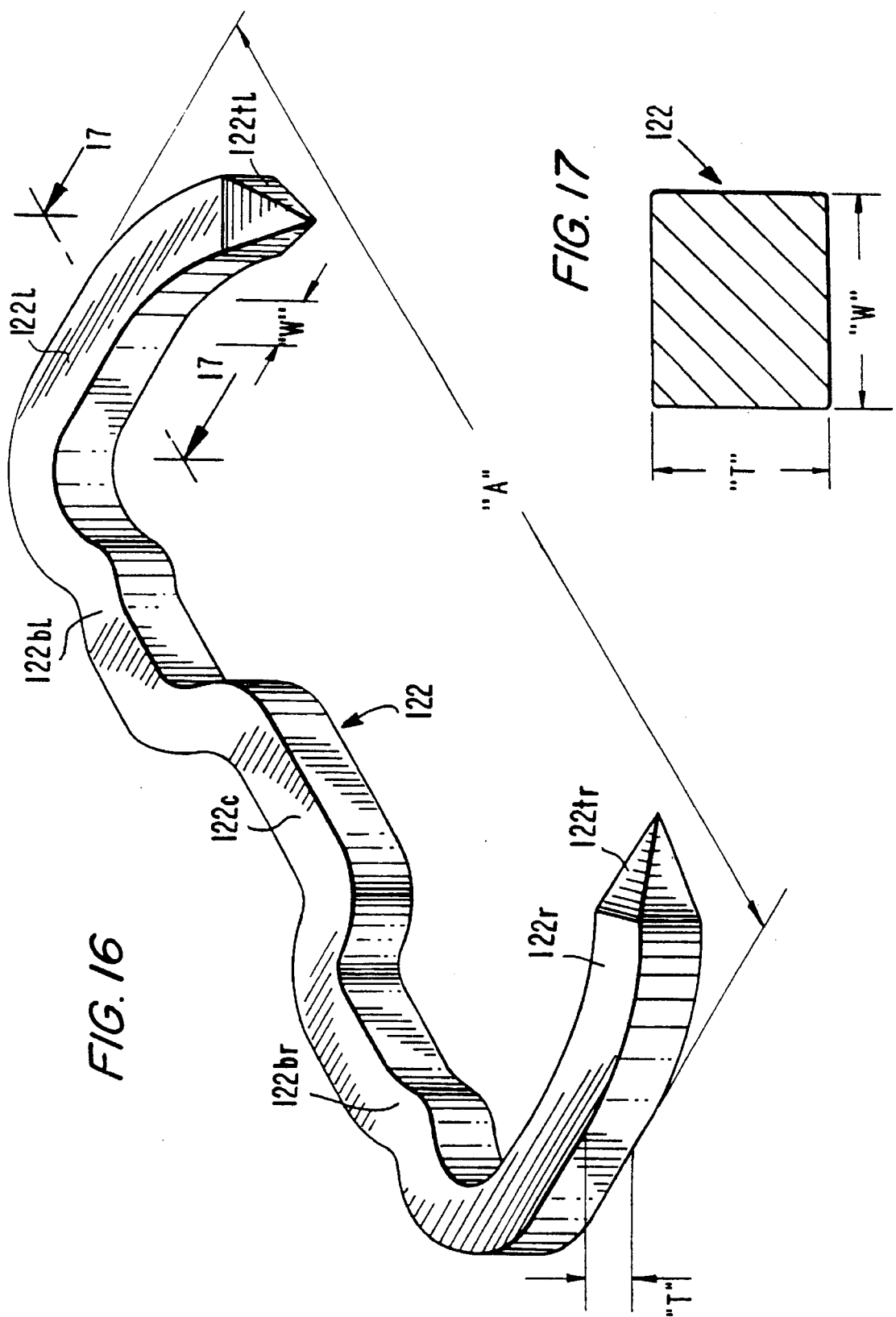

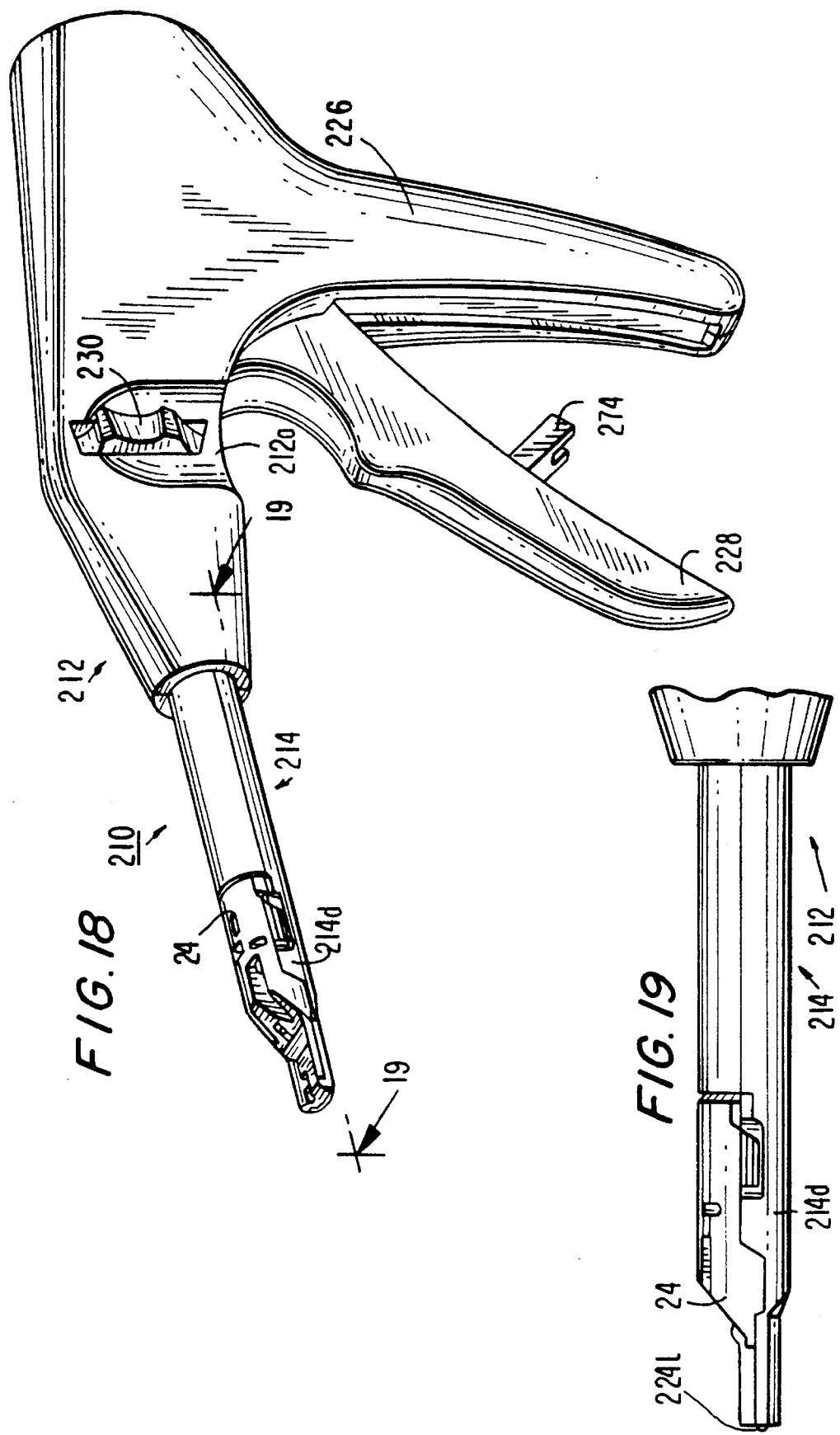

APPARATUS AND METHOD FOR APPLYING SURGICAL STAPLES TO BODY TISSUE

BACKGROUND OF THE INVENTION

1. Field of the Invention

The present invention relates to an apparatus and method for applying surgical staples to body tissue and to attach objects to body tissue.

2. Description of the Related Art

Surgical repair of body organs and tissue in general often requires the application of surgical fasteners. In some instances, the fasteners used are in the form of two part fasteners and in other instances, they are unitary metal staples. Such metal staples are used in numerous types of body tissue repair including such procedures as chest wall reconstructions, tram flap procedures, hernia repairs, etc. In most surgical repairs, the staples are applied directly to the body tissue requiring attachment or reattachment. In certain other procedures, the staples are used to attach an intermediate object to the body tissue. One such example is the application of surgical mesh to body tissue which is often used in hernia repairs.

For example, the surgical repair of hernias is generally confined to the lower abdominal and groin area of the body, involving repositioning and reattachment of the herniated portion of the abdomen using surgical staples or sutures. Developments in laparoscopic and endoscopic surgery have enabled surgical procedures to be performed in certain confined areas. In addition, surgical repairs involving other body parts or organs have also benefitted from laparoscopic and endoscopic advances.

One elongated surgical stapler for endoscopic applications is described in commonly assigned U.S. patent application Ser. No. 07/950,425, filed on Sep. 23, 1992 which is incorporated herein by reference. The aforesaid elongated surgical stapler comprises frame means, generally elongated endoscopic means, means for storing a surgical staple, means for individually advancing the staple distally, and anvil means for closing the staple to attach the staple into body tissue.

Non-endoscopic hernia procedures may also entail surgery in the confined areas of the lower or upper abdomen. Instruments which are relatively short in length may be utilized for direct insertion into the lower abdomen through surgical incisions. Once the surgical stapler is inserted, it would be advantageous to provide a surgical stapler whereby the distal end of the stapler articulates relative to an axis of the stapler for extending the distal end around bones, body tissue, and the like to orient and apply surgical staples from the distal end into body tissue. These staples could be applied directly to body tissue or for attaching objects such as mesh to body tissue. A need, therefore, exists in many such procedures for a compact surgical stapler having an articulating distal end employing few moving parts for accurately positioning and securely attaching surgical staples to body tissue without danger of separation thereof after attachment is completed.

In addition, the articulation mechanism should provide a stable articulated position at the distal end, allowing the distal end to be set in a fixed orientation by the operator as the operator directs the his/her hands to other activities.

In such staple applications where the surgical staples are secured to the body tissue or mesh (depending upon the particular procedure) by advancing the staple using a pusher plate distally into the body tissue/mesh and forming the staple about the anvil structure, it would be particularly advantageous for the pusher plate to have a structure to apply pressure to a backspan of the staple in a manner to inhibit bending thereof. Moreover, the anvil structure would cause the staples to bend in an improved fashion if it included curved surface portions for engagement with the fasteners.

The present invention relates to an apparatus for applying staples to body tissue in numerous types of procedures where improved access to the body tissue is required.

In particular, the present application incorporates a relatively uncomplicated system for articulating the staple cartridge while providing uniform and continuous advancement of staples for application to body tissue consistent with the above-noted objectives.

SUMMARY OF THE INVENTION

Apparatus is disclosed for applying at least one surgical fastener to body tissue, which comprises a frame and a tubular member connected to the frame and extending distally therefrom having a generally longitudinal axis, a proximal end portion, and a distal end portion. At least one surgical fastener such as a surgical staple is supported by the tubular member, and means is provided for advancing the at least one surgical fastener distally for positioning adjacent the body tissue. Articulating means provides for pivotally rotating the distal end portion to predetermined angles with respect to the generally longitudinal axis, and the articulating means including rotatable means rotatable about an axis generally transverse to the longitudinal axis.

The fastener is supported by a fastener storing means removably supported by the tubular member. A collar positioned about a proximal portion of the tubular member moves longitudinally in proximal and distal directions to control the pivoting of the distal end portion. The collar is movable to at least one staple position which corresponds to a predetermined pivot angle of the distal end portion relative to the longitudinal axis.

The apparatus also comprises means for closing the surgical fastener, and the fastener advancing means comprises a spring channel member defining a channel dimensioned and configured to allow at least one surgical fastener to pass therethrough. The spring channel member has resilient means for moving a closed surgical fastener upwardly from the fastener closing means to release the closed surgical fastener. The spring channel member includes a projection for preventing a surgical fastener from moving in a proximal direction.

The fastener is positioned in a cartridge and the articulating means comprises a collar member mechanically connected to pivotally rotate the cartridge and adapted to retain the cartridge at a 0° angle relative to the longitudinal axis when the collar member is located at a predetermined distalmost position. The collar member is movable to at least a second position proximal of the first position to effect pivotal movement of the cartridge to an angle of about 45° relative to the longitudinal axis of the tubular member.

The rotatable means comprises a disc-like member for mechanically connecting the collar member and the cartridge in a camming relationship. The disc-like member includes means for setting the cartridge at a predetermined angle relative to the longitudinal axis of the tubular member. At least one rod is provided and is mechanically connected to the cartridge with a camming surface of a detent of the disc-like member to longitudinally move the rod for pivoting the cartridge.

The tubular member comprises a cartridge support member for releasably retaining the cartridge, where the fastener is positioned in the cartridge retained in a cartridge support member. The fastener closing means includes an anvil having at least two projections and the cartridge support includes an aperture for correspondingly locating the projection of the closing means to position the closing means substantially adjacent the cartridge support. The anvil includes at least two upstanding staple closing anvil members each having a proximal curved surface corresponding to similar distal curved surfaces on the backspan of a surgical fastener.

A first aperture and first projections are located at a distal portion of the cartridge support and closing means, respectively. A second aperture and second projections are located at a proximal portion of the cartridge support and closing means, respectively.

The cartridge support member also includes a projection for positioning a portion of the anvil substantially adjacent the cartridge support. Similarly, the anvil includes an aperture for correspondingly locating the projection of the cartridge support to position the closing means substantially adjacent the cartridge support. An anvil for closing the at least one surgical staple is provided, and a rotatable member having at least one slot allows for selectively pivoting the distal end portion of the tubular member to predetermined angles with respect to the longitudinal axis of the tubular member.

The plurality of surgical staples are stored in a cartridge connected to support means pivotally attached at the distal end portion of the tubular member. The support means is selectively pivotal by the articulating means such that the cartridge is pivotal therewith, and the articulating means includes control means to pivot the cartridge from a proximal location. The staple advancing mechanism includes at least two distal projections for applying pressure to a backspan of the at least one surgical staple to close the staple by the anvil in a manner to prevent the backspan from bending. The staple advancing mechanism also includes a gap formed between the at least two distal projections for providing relief to the pusher to slide smoothly over the anvil. At least two upstanding legs are provided on the anvil for closing the at least one surgical staple while applying same to body tissue, and the legs each include a rounded portion for forming and closing the at least one surgical staple therearound.

A spring channel is included for passage of the at least one surgical staple and having an upwardly biased resilient member for lifting each the staple upwardly from the anvil after formation therearound. A cartridge storing the surgical staples is supported on a pivotally mounted cartridge support member having at least two distally extending tabs engaging body tissue for stabilizing the cartridge relative to the body tissue during application of the staples.

BRIEF DESCRIPTION OF THE DRAWINGS

Preferred embodiments of the invention are described hereinbelow with reference to the drawings wherein:

FIG. 1 is a perspective view from above of an apparatus constructed according to the present invention for applying surgical staples to body tissue;

FIG. 2 is a side elevational view of the distal portion of the apparatus of FIG. 1 for pivoting a staple cartridge support member;

FIG. 3 is a perspective view, with parts separated for illustration purposes, of the handle of the instrument of the invention and the associated components;

FIG. 4 is a perspective view, with parts separated for illustration purposes, of the staple advancing system and cartridge articulating control mechanism with components thereof;

FIG. 9 is a side elevational view of the anvil member shown in FIG. 8;

FIG. 10 is a top plan view of the spring channel member shown in FIG. 8;

FIG. 11 is a cross-sectional view taken along lines 11—11 of FIG. 1 illustrating the distal end portion of the instrument including the pivotal staple cartridge support system;

FIG. 12 is a view taken along lines 12—12 of FIG. 11 illustrating the distal end of the instrument of FIG. 1;

FIGS. 13–15 are views from above of the distal end portions of the instrument of FIG. 1 in various stages of engaging and forming of a surgical staple to a formed position;

FIG. 16 is a perspective view of the staple of the present invention;

FIG. 17 is a cross-sectional view taken along lines 17—17 of FIG. 16;

FIG. 18 is a perspective view from above of an alternative embodiment of the apparatus of the present invention for applying surgical staples to body tissue; and FIG. 19 is a side elevational view of the distal end of the apparatus in FIG. 18.

DETAILED DESCRIPTION OF THE PREFERRED EMBODIMENTS

GENERAL

Figure 5:
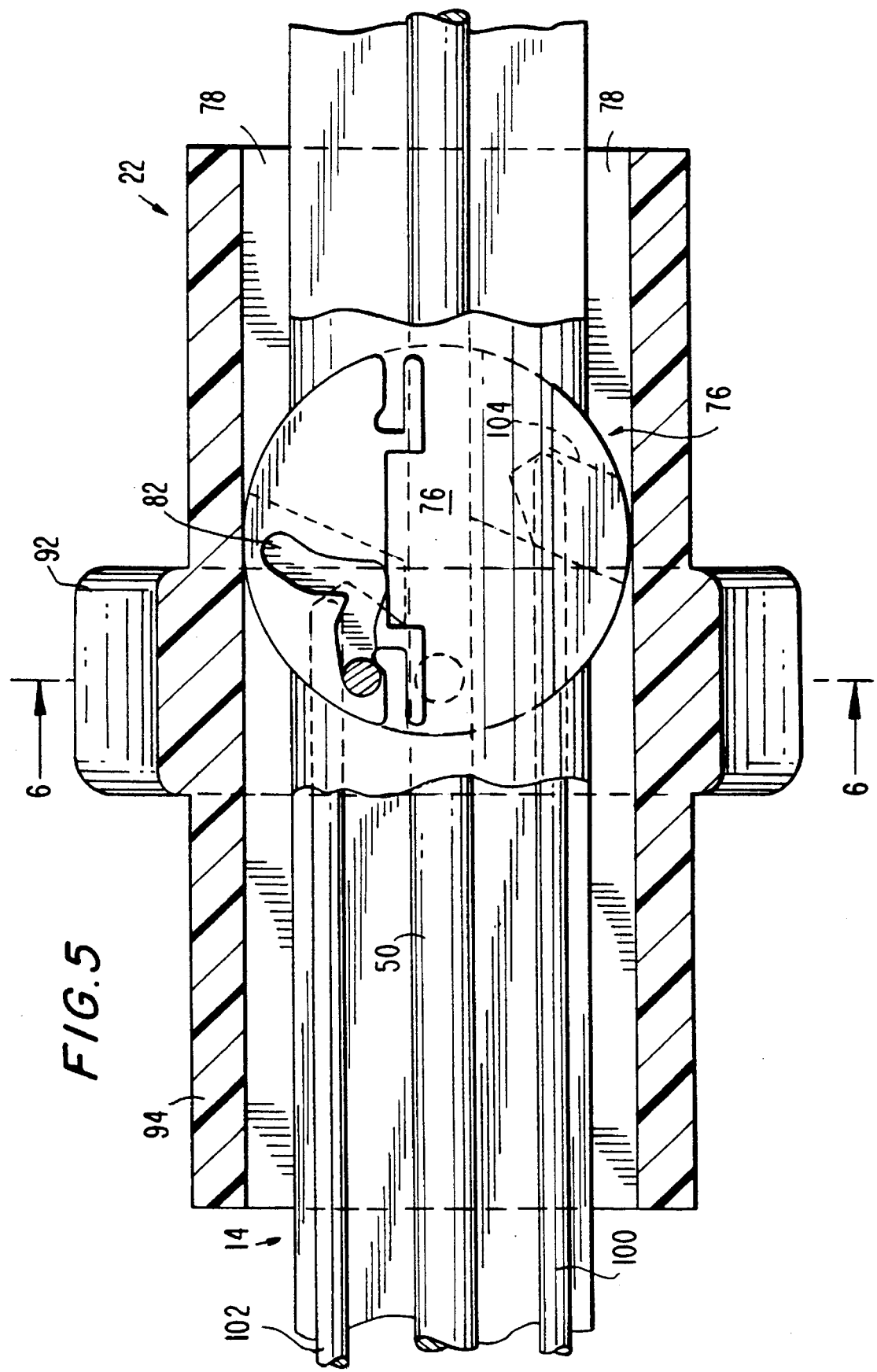
FIG. 5 is a cross-sectional view taken along lines 5—5 of FIG. 1 illustrating the articulating control mechanism in a first position.
Figure 6:
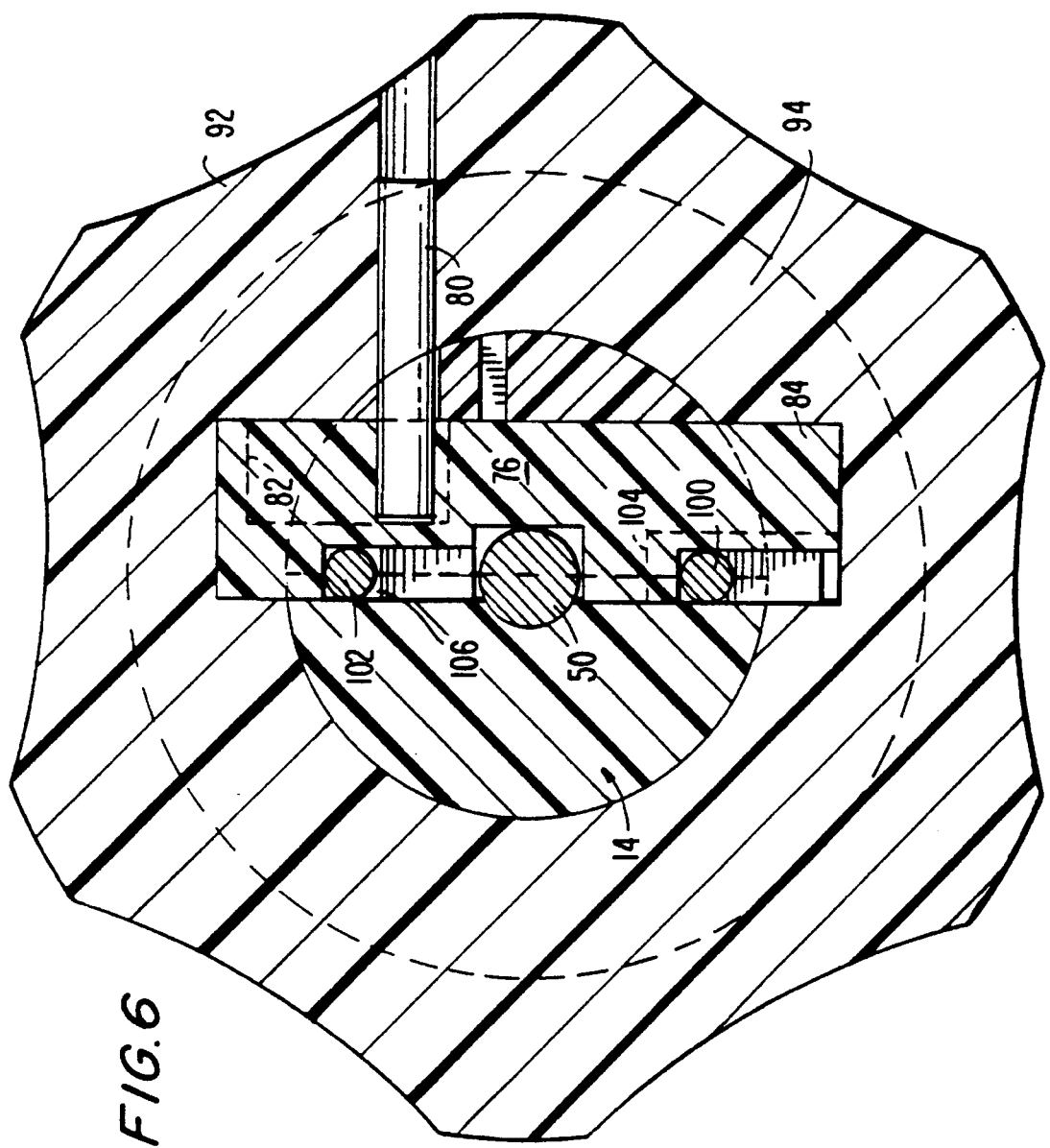
FIG. 6 is a cross-sectional view taken along lines 6—6 of FIG. 5 illustrating further details of the mechanism for providing pivotal motion to the staple cartridge support member at the distal end portion.

Following is a general description of the present instrument, the description is divided into separate sections to describe the structure and the desired movements produced thereby. Those sections include the handle section, the staple cartridge support pivoting system, the tubular section, the staple firing system, the staple cartridge support member, and the staple closing system. An alternative embodiment of the invention is described thereafter.

THE INSTRUMENT

Referring initially to FIG. 1 there is illustrated in perspective view the apparatus 10 particularly adapted for applying surgical staples to body tissue. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) may also be utilized. However, equivalent alternative materials will readily come to the mind of those skilled in the art.

The apparatus 10 includes handle portion 12, tubular section 14 having a distal end portion, and a cartridge support section 18 which supports a removable staple cartridge 24. The cartridge support section 18 includes flange 16 to which horizontal staple cartridge support member 20 is attached. Flange 16 is pivotally attached to tubular section 14 by pins 21 to permit the combination of staple cartridge support member 20 and cartridge 24 to pivot with respect to at least one side of the longitudinal axis extending centrally through the tubular section 14 as shown in FIG. 2. Generally, in this embodiment the staple cartridge support member 20 may be selectively pivoted up to about 45° with respect to the aforesaid longitudinal axis. In the illustration of FIG. 1 the staple cartridge support member 20 is shown in general alignment with the longitudinal axis of the tubular section 14 and in phantom lines in FIG. 2 to illustrate a range of movement.

Referring generally to FIG. 1, the handle 12 of instrument 10 includes manual grip 26 and pivotal trigger 28 which is pivoted toward and away from manual grip 26. Trigger 28 is pivoted toward manual grip 26 during the staple advancing and firing sequence which are described in further detail below. Trigger 28 pivots away from manual grip 26 to return the instrument to the pre-fired condition in position for firing the staple next in line.

Referring again to FIG. 1, a first manually operative star wheel 30 is rotatable and adapted to rotate the staple cartridge support member 20 a full 360° as described hereinbelow, while proximal movement of a collar 22 including a second manually operative star wheel 32 produces pivotal motion of the staple cartridge support member 20 to one of the positions shown in phantom lines in FIG. 2. First star wheel 30 is conveniently positioned within handle frame 12 which includes relief 12a to permit access to the first star wheel 30 by a user's fingers.

To achieve other pivotal positions, the first star wheel 30 may be simply rotated 180° thereby rotating the staple cartridge support member 20 and causing the position of the staple cartridge support member 20 to be reversed. Thus, it can be seen that the combination of full rotation and the pivotal movement of the staple cartridge support member 20 facilitates a wide range of articulation of the distal end of the staple cartridge support member 20, thus facilitating application of staples over a wide range of locations (±180°) and in any of a plurality of orientations. In the embodiment of the invention shown in the accompanying Figs. incorporated herein, articulating means to accomplish articulation of the staple cartridge support member 20 and the staple cartridge 24 is described. Such articulation means includes proximally located control means comprising collar 22 such that, when the collar 22 is moved to its proximalmost position, the staple cartridge support member 20 is in one of the positions shown in phantom lines in FIG. 2, e.g. at an angle of approximately 45° with respect to the longitudinal axis of the instrument 10. When the collar 22 is advanced to the distalmost position, the staple cartridge support member 20 assumes the position shown in FIG. 1, i.e. in alignment with the longitudinal axis of the instrument 10.

Thus, in the preferred embodiment of FIG. 1, it can be seen that a full 90° of pivotal movement of the staple cartridge support member 20 may be achieved simply by longitudinal movement of collar 22 in combination with full rotation of the staple cartridge support member 20 by first star wheel 30. The longitudinal movement of collar 22 causes pivotal movement of the staple cartridge support member 20 to 45° in one direction and rotation of the staple cartridge support member 20 provides effective completion of the articulation of the staple cartridge support member 20. Both of these movements in combination facilitate a wide range of maneuverability of the distal end of the staple cartridge support member 20, thus facilitating application of staples over a wide range of locations (±180°) and in any of a plurality of orientations.

The instrument can also be configured to articulate, i.e. pivot, staple cartridge support member 20 to positions other than a 45 degree angle with respect to the longitudinal axis of the instrument which extends through handle portion 12 and centrally of the tubular section 14. For example, the instrument 10 can be configured to articulate to a 20° or a 65° angle.

In an alternative preferred embodiment, the first star wheel 30 can be eliminated and the star wheel 32 can be utilized to rotate the cartridge support member 20 with the tubular section 14 a full 360° to achieve substantially multi-directional staple application capability.

THE HANDLE SECTION

Referring to FIG. 3, there is shown a perspective view, with parts separated for illustration purposes, of the handle 12 of the instrument with associated components. The handle 12 is comprised of an outer housing preferably formed of separate sections as shown of polycarbonate material. The separate parts shown are attached by welding, adhesives, etc. The ultimate purpose of the handle mechanism is to provide controlled distal movement to the proximal staple advancing tube 34 of the pusher assembly, a portion of which is shown in FIG. 3. Trigger 28 is pivotally mounted to housing 26 by pivot pin 60. Pin 37 is attached to the proximal end of trigger 28 and slidably engages a proximal camming surface 36a of a triangular shaped portion of pivoting member 36 which pivots at a lower end of the handle 12 about pin 62. Proximal staple advancing tube 34, which is rotatably engageably received within the upper aperture 39 of pivoting member 36 rotates within the upper aperture 39 as first star wheel 30 is rotated.

As illustrated in FIG. 4, firing rod 50 is connected to proximal staple advancing tube 34 and extends through the tubular section 14, a portion of which is shown in phantom lines in FIG. 3. In the embodiment shown, the first star wheel 30 is intended to be permanently and rotatably attached to the instrument 10 via sleeve 38 having rim 40 slidably positioned within appropriately configured relief compartments in the handle 12 shown generally at 12b. The sleeve 38 frictionally engages tube 42 which is proximally biased against first star wheel 30 by spring 44. Tube 42 includes proximal tabs or rachet teeth for frictionally engaging corresponding distal tabs (not shown) or rachet teeth of first star wheel 30. The first star wheel 30 protrudes through apertures 46 on either side of handle 12. Rotation of the first star wheel 30 thus causes the corresponding rotation of the firing rod 50 ultimately to rotate the staple cartridge 24 about its own axis (i.e, an axis extending centrally therethrough) as will be described in detail hereinbelow. In the embodiment where rotation is achieved by star wheel 32, star wheel 30 and the relief aperture 46 are eliminated. Thus, the outer surface of handle 12 will be relatively smooth.

Additionally, in the embodiment utilizing first star wheel 30, a clutch ratchet mechanism for the handle 12 is positioned within the rotation mechanism. More specifically, in this embodiment, pawl 48 is pinned for rotation to the proximal staple advancing tube 34 attached to firing rod 50 shown in FIG. 4. Pawl 48 is attached to staple advancing tube 34 by pin 52 such that when pawl 48 is in engagement with ratchet plate 54 positioned within the tubular section of the first star wheel 30, rotation of first star wheel 30 also causes rotation of proximal staple advancing tube 34 as well as firing rod 50. Pin 52 extends from a distally located aperture 53 on the tubular section of the first star wheel 30, through spring 56 and pawl 48 on pins 57, 59 extending from the distal end of the proximal staple advancing tube 34, as shown in FIG. 3. Pin 52 then extends into aperture 58 in firing rod 50, as shown in FIG. 4, and through an aperture in the proximal staple advancing tube 34. Thus, when pawl 48 is in engagement with ratchet plate 54 positioned within the cylindrical section of the first star wheel 30, rotation of the first star wheel 30 causes rotation of the staple advancing system.

As described hereinabove, rotation of the staple advancing system thereby causes corresponding rotation of the staple cartridge support member 20 which includes the exemplary angles illustrated in FIGS. 1–2. Other suitable fastening techniques may be utilized. In the embodiments of FIGS. 1–2, rotation to any angle up to 360° and beyond is possible independent of the pivotal angle of the staple cartridge support 20 by simply rotating the first star wheel 30.

The instrument shown is contemplated to be entirely disposable. It is also contemplated and within the scope of the invention to construct the tubular section 14 to be selectively detachable whereby the handle 12 may be sterilized and reused, or the tubular section 14 can be sterilized, and the staple cartridge support member 20 re-loaded with staples for re-use. Alternatively a replacement staple cartridge 24, and optionally a replacement tubular section 14, may be detachably secured to a disposable handle 12 for multiple use during a single surgical procedure.

Referring again to FIG. 3, trigger 28 is pivotally attached by a pivot pin 60 for pivotal movement toward and away from the handle grip 26, and is adapted to produce rotational movement of pivoting member 36. Thus, it can be seen that when handle grip 26 is positioned in the palm of the user's hand and trigger 28 is squeezed toward the handle grip 26, pivoting member 36 rotates in a counterclockwise direction while the upper portion of the pivoting member 36 pivots forwardly about a point of rotation defined by a pivot pin 62 located at the lowermost end of the handle grip 26 shown in FIG. 3.

As can be seen in FIG. 3, the pusher assembly is connected to the upper portion of the pivoting member 36 through an aperture such that inward squeezing of trigger 28 causes the entire pusher assembly to advance distally against the constant force provided by negator spring 64 as shown. The negator spring 64 is formed of a resilient flat spring material coiled about a rotational bar 66 which is rotationally mounted about a cross member of bracket 68.

The free end of negator spring 64 is attached to an anchor pin 70 via an aperture 72 as shown, while the negator spring 64 is normally biased toward the coiled configuration as shown in FIG. 3. It can therefore be appreciated that, after squeezing trigger 28 in a full stroke from the position shown in FIG. 3 toward handle grip 26, a release of the trigger 28 permits the negator spring 64 to assume control and to return rotational bar 66 to the pre-fired proximal location by the automatic winding action of the negator spring 64 to its original unloaded configuration. This motion in turn causes the entire pusher assembly to return to the proximalmost pre-fired position as shown in FIG. 1. The constant force of negator spring 64 uniquely prevents the natural tendency of the user to rotate his/her hand as springs increase in force when progressing through a full spring cycle.

Referring to FIGS. 1 and 3, trigger stop device 74 is attached to trigger 28 and is configured and dimensioned for engagement with handle grip 26 in a manner to thereby limit the proximal pivotal movement of trigger 28. Depending upon the particular limits required in the apparatus, trigger stop device 74 can be dimensioned accordingly.

The structure and function of the uni-motion clutch mechanism will now be described. This clutch mechanism prevents proximal movement of the pusher assembly in the event the trigger mechanism is released after the squeezing motion of the trigger mechanism and the advancement of the pusher assembly has begun but before the full stroke is completed. The clutch mechanism is self-releasing when the pusher assembly reaches the distalmost position, thus permitting the entire pusher assembly to return to the pre-fired, or proximalmost condition, and the trigger mechanism to also return to the pre-fired position.

Referring once again to FIG. 3, ratchet plate 54 is fixed to the interior surface of the first star wheel 30 and therefore fixed with respect to the handle housing. The rachet plate 54 possesses a surface defined by a plurality of right angle triangular shaped parallel ridges. Pawl 48 is rockably mounted for distal and proximal movement with proximal staple advancing tube 34 through the interior of first star wheel 30, and is biased toward ratchet plate 54 by resilient wire spring 44 as shown. The pawl 48 is preferably of stainless steel while ratchet plate 54 is made of brass or other compatible material.

While trigger mechanism 28 is squeezed toward handle grip 26 producing distal motion of the entire pusher assembly, pawl 48 engageably slides distally past the ratchet surface of ratchet plate 54 such that one corner of the tip of the pawl 48 sequentially engages each right angled ridge of ratchet plate 54 to thereby prevent proximal movement of the pusher assembly in the event the trigger mechanism is released by the operator. The engagement of pawl 48 with ratchet plate 54 provides audible confirmation that the pusher assembly is moving distally since the user hears a series of progressive audible clicks. This action continues with the tip of pawl 48 sliding past the ratchet surface of the ratchet plate 54 until the pawl 48 is positioned distally of the distalmost tooth.

After completion of the staple firing stroke and upon release of the trigger mechanism 28, the pawl 48 moves proximally with the pusher assembly as described under the action of negator spring 64. An end portion of pawl 48, which is now free, engages the distal end of the ratchet plate 54 causing the pawl to rock to the reverse direction so as to slide proximally past the ratchet surface of ratchet plate 54 without interference to the proximal movement of the pusher assembly. Thus, it can be seen that the clutch mechanism as described effectively permits squeezing the trigger mechanism 28 toward the handle grip 26 while maintaining all positions midway through the stroke in the event the operator releases the grip, and also permitting return motion thereof after the stroke has been completed. The clutch mechanism also allows the operator to advantageously preposition a staple such that the legs of the staple protrude from the distal end of the staple cartridge support member discussed hereinafter, and then to release pressure from the trigger mechanism. The operator may then turn full attention to locating the prepositioned staple in the desired target location, at which point the pivoting of the trigger mechanism may be resumed and the cycle completed. This staple prepositioning facilitates staple placement.

THE TUBULAR SECTION

For purposes of the present description, the tubular section 14 and related components contained therein is described as the section shown in FIG. 4 extending from the handle 12 to the flange 16 pivotally attached thereto at the distal end and having the staple cartridge support member 20 extending distally from flange 16. However, it is clear that reference to the tubular section 14 may contemplate the section shown, with or without the staple storage section or support member 20 and the flange 16 included.

Referring now to FIG. 4 in conjunction with FIGS. 1–3, a pusher assembly is positioned within and extending through the tubular section 14 and includes proximal staple advancing tube 34 connected to firing rod 50 extending through the tubular section 14 to the distal end. In FIG. 4, the tubular section 14 is shown in a perspective view with parts separated for convenience of illustration and includes first housing half section 14a and second housing half section 14b. The housing half sections 14a, 14b are preferably of a polycarbonate material such as LEXAN brand material mentioned previously, and are attached by welding, adhesives, etc. Positioned within the housing half sections 14a, 14b is the pusher assembly as described in more detail below.

Figure 7:
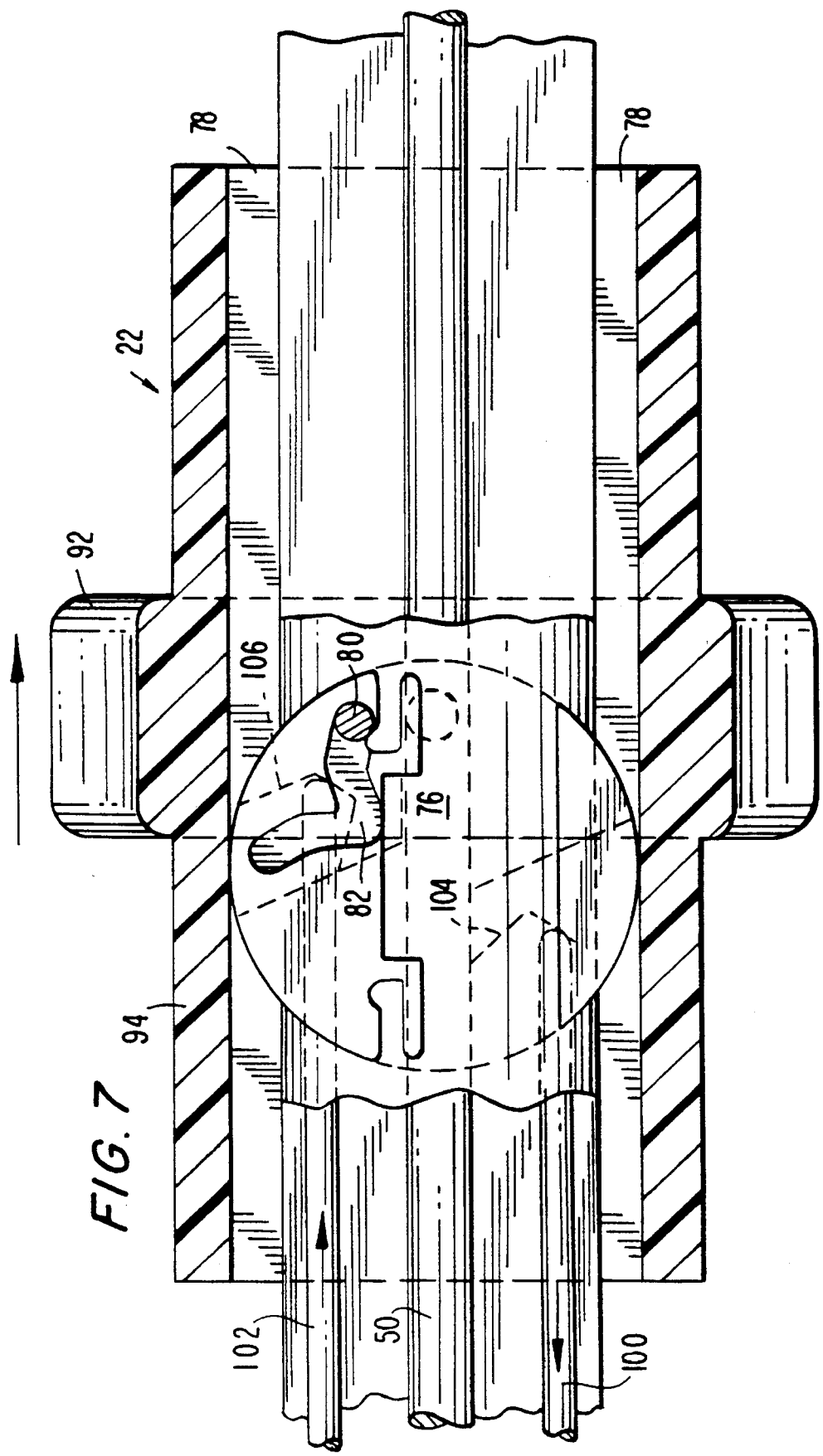
FIG. 7 is a cross-sectional view of the articulating control mechanism of FIG. 5 shown in a second position.

Referring in particular to FIGS. 4–5, collar 22 is structured and dimensioned to receive rotatable means comprising disc 76 so as to slidably engaging longitudinal interior grooves 78 of collar 22 and rotating between a range of angles, as illustrated in FIGS. 5 and 7. Pin 80 extends through an aperture in collar 22 and through wing shaped aperture 82 in side portion 84 of disc 76 to slidably engage aperture 82 and to key these components together for common distal and proximal movement.

The disc 76 has an upper portion 86 and rotates within apertures 88, 90 of housing half sections 14a, 14b. A second star wheel 32 is positioned on and is preferably integral with a tubular portion 94 of collar 22 so that collar 22 is thus conveniently movable longitudinally and rotatably by the user when the second star wheel 32 is gripped between the user's fingers. Collar 22 is rigidly connected to tubular section 14 via disc 76 and pin 80 as will be described in further detail. Accordingly, manual rotation of collar 22 causes corresponding rotation of tubular portion 14. However, the operator need not grip the collar 22 at any specific locations.

A pusher plate 96 is rotatably attached to flexible firing wire 98 which is in turn attached to the distal end of the firing rod 50. Drive rods 100, 102 extend through the tubular section 14, having proximal ends which engage multifaceted apertures in disc 76 (shown in FIGS. 5 and 7), and distal ends which engage the proximal end of the flange 16 to pivot the flange 16 by proximal or distal motion of the drive rods 100, 102.

The operation of the system to effect pivotal movement of the flange 16 and attached staple cartridge support member 20 is now described. When collar 22 is in the distalmost position, the staple cartridge support member 20 is at 0° relative to the longitudinal axis of the tubular section 14; i.e. in line with the tubular section 14 as shown in solid lines in FIGS. 1–2. In this position, pin 80 is engageably nestled at a distal end of the wing shaped aperture 82, as shown in FIG. 5. The proximal end of the first drive rod 100 is positioned against a first facet of multifaceted aperture 104, and the proximal end of the second drive rod 102 is positioned against a first facet of multifaceted aperture 106. Note that the distal end of the wing shaped aperture 82 prevents further relative motion of the disc 76 within grooves 78 so further distal motion of the collar 22 is restricted.

Referring now to FIG. 7 in conjunction with FIGS. 4–5, the mechanical movements required to produce pivotal movement of the staple cartridge support member 20, flange 16, and staple cartridge 24 will now be described. When collar 22 is moved proximally by hand, this movement in turn results in relative movement of pin 80 to the midpoint of the wing shaped aperture 82. The curved shape of the aperture 82 having detents causes pin 80 to remain at the midpoint with no further motion by the operator; i.e. the midpoint is a stable position for pin 80. With the pin 80 at the midpoint, proximal or distal motion of the collar 22 by the operator moves the pin 80 out of the midpoint position.

From the midpoint position, further proximal motion of collar 22 causes clockwise rotation of disc 76 resulting in the relative movement of pin 80 to the proximalmost position in the wing shaped aperture 82 as illustrated in FIG. 7. The proximal end of aperture 82 prevents further rotating motion of the disc 76 in grooves 127, so that further proximal motion of the collar 22 is restricted. This position corresponds to the staple cartridge support member 20 and the staple cartridge 24 articulated to an angle of about 45° with respect to the longitudinal axis.

Referring further to FIGS. 5 and 7, the shape of the aperture 82 causes the operator to feel when the pin 80 attains the midpoint position in the aperture 82; i.e. the operator feels a detent, or slight hesitation of movement, by the collar 22. The location of the pin 80 at the distalmost end and at the proximalmost end of aperture 82 correspond to the staple cartridge support member 20 pivoted and stabilized at about 0° and about 45° to the longitudinal axis, respectively, as explained in further detail below.

Referring again to FIG. 5, the pin 80 is at the distalmost end of the wing shaped aperture 82, and drive rods 100, 102 are positioned in respective multifaceted apertures 104, 106 corresponding to the staple cartridge support member 20 (shown in FIG. 1) positioned at 0° relative to the longitudinal axis of the tubular section 14. Proximal motion of collar 22 moves pin 80 toward the proximal end of the aperture 82, causing disc 76 to rotate clockwise producing a camming motion. The rotation of the disc 76 rotates the multifaceted apertures 104, 106 formed on the back side of disc 76 as shown as dotted lines in FIG. 5. Thus, the facets of multifaceted aperture 104 push drive rod 100 distally in a camming action. Simultaneously, the facets of the multifaceted aperture 106 rotate away from drive rod 102 to allow drive rod 102 to move proximally as flange 16 pivots in a clockwise rotation to a position such as shown in FIG. 2.

Referring to FIG. 11, the distal ends of drive rods 100, 102 are positioned substantially adjacent to flange 16, so distal motion of drive rod 100 rotates the staple cartridge support member 20 clockwise about a pivot pin 21.

Similarly, equal and oppositely withdrawing drive rod 100 accommodates the downward movement of the flange 16. In a similar fashion when the collar 22 in FIGS. 4–7 is moved in the opposite distal direction, the movement of each drive rod 100, 102 is respectively reversed causing drive rod 102 to move distally and to engage the flange 16 and drive rod 100 withdraws to accommodate the pivotal movement of staple cartridge support member 20 back to the original (or neutral) position in general alignment with the tubular section 14 as shown in FIGS. 1 and 11. The subsequent distal motion of collar 22 releases the pushing pressure of the facets of the multifaceted aperture 104 against drive rod 100, and also causes the facets of the multifaceted aperture 106 to move drive rod 102 distally in a camming action. The distal motion of drive rod 102 pivots flange 16 counterclockwise, where sufficient distal motion of the collar 22 returns the flange 16 to the 0° position as shown in FIGS. 1 and 11.

The distal end of drive rods 100, 102 may abut the flange 16 to pivot the flange 16 by the above described reciprocating longitudinal motion of the drive rods 100, 102. Alternatively, the distal ends of drive rods 100, 102 may be mounted into flange 16, with a distal portion of the drive rods 100, 102 being resilient to bend as the flange 16 pivots.

Alternatively, one rod may be provided and connected to the staple cartridge support member 20 and adapted to pivot the staple cartridge support member 20 by causing such rod to move proximally and distally thereby actuating the pivoting of the staple cartridge support member 20 about the pivot point.

THE STAPLE FIRING SYSTEM

Figure 8:
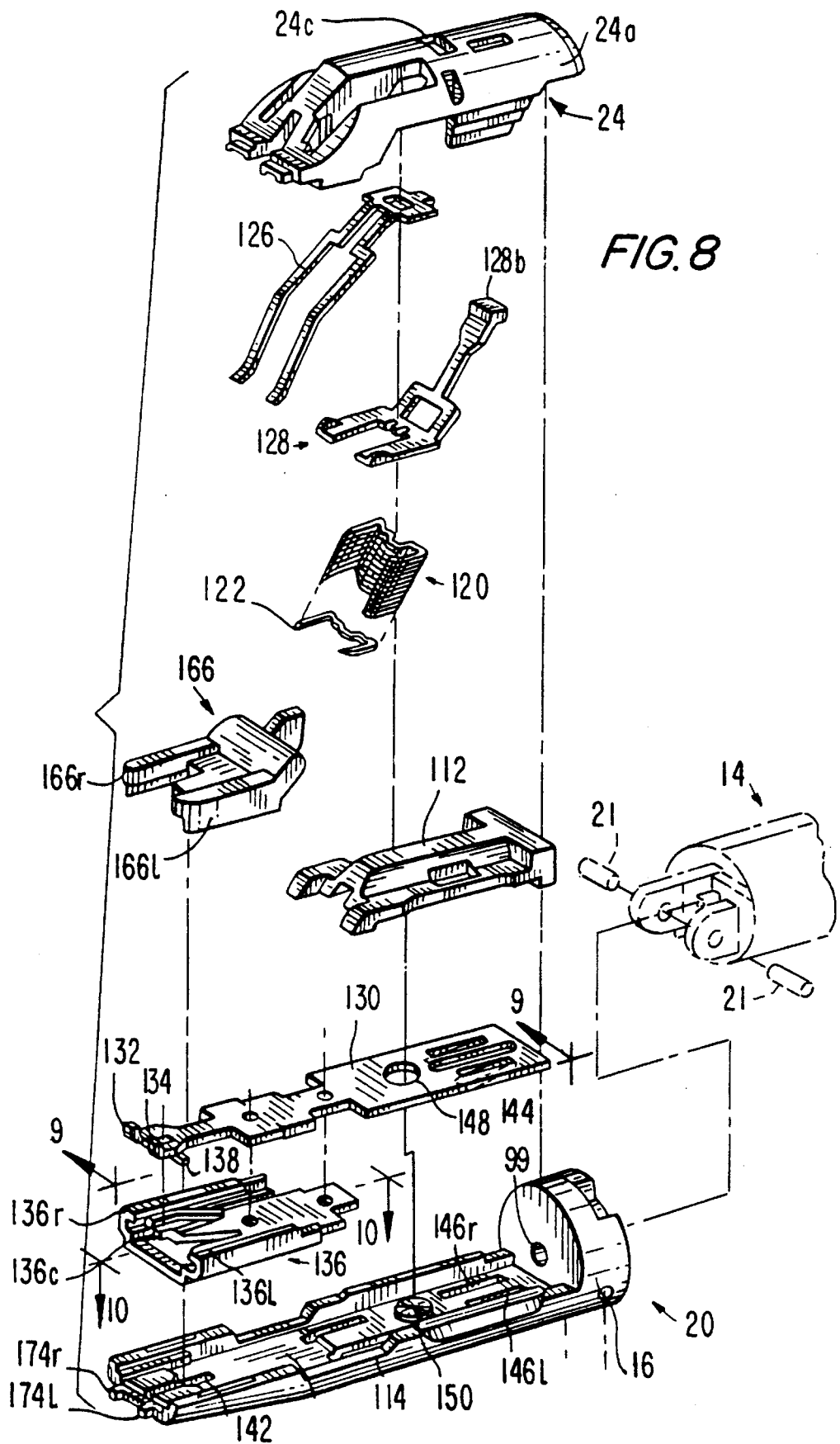
FIG. 8 is a perspective view, with parts separated for illustration purposes, of the distal end portion of the instrument including the pivotal staple cartridge support system.

Referring now to FIGS. 8 and 11 in conjunction with FIG. 4, the pusher assembly includes firing rod 50 connected to flexible elongated firing wire 98 extending through aperture 99 and which is in turn connected to pusher plate 96 as shown. The connection between firing rod 50 and firing wire 98 is a crimped or swaged connection, whereas the connection between firing wire 98 and pusher plate 96 is accomplished by an interference fit between the firing wire tip 108 and bent portion 110 which is attached to pusher plate 96 as illustrated in FIG. 11. In an embodiment described hereinbelow, swaging of the bent portion 110 to firing rod 50 is utilized. Firing rod 50 and pusher plate 96 are preferably made of stainless steel whereas firing wire 98 is made to be resiliently flexible to accommodate the pivotal movement of the staple cartridge support member 20 and flange 16 since firing wire 98 is located at the distal end of the instrument 10. Rotation of the firing rod 50 by first star wheel 30 rotates the attached resilient firing wire 98 and the pusher plate 96 connected thereto. Since the pusher plate 96 is nestled within the staple cartridge support member 20, rotation of the proximalmost first star wheel 30 thus causes rotation of the flange 16 and, therefore, the staple cartridge support member 20 about its own axis. It will be appreciated that when the staple cartridge 24 is articulated to the angle about 45°, the firing wire 98 will be subjected to resilient flexing in alternating bending modes.

As seen particularly in FIG. 11, pusher plate 96 is attached by upwardly bent U-shaped fastener 110 which contains apertures in the distal and proximal walls thereof for reception of the distal tip 108 of the elongated super elastic metal firing wire 98. The wall portions defining these apertures are swaged for permanent attachment to the super elastic firing wire 98 which is in turn attached to firing rod 50 by insertion into a central opening at the distal end and swaging the metal tubular portion inwardly for attachment to the super elastic firing wire 98. The super elastic firing wire 98 is preferably TINEL brand metal available from Raychem Corporation, Menlo Park, Calif. As noted hereinabove, another example of such super elastic firing wire is NITINOL brand metal. Other materials are also contemplated for firing wire 98.

THE STAPLE CARTRIDGE SUPPORT SECTION

Referring now to FIGS. 8–12, the staple cartridge support section 18 is illustrated at the distal end of the instrument 10. In FIG. 11 the staple cartridge support member 20 is shown in the position generally in alignment with the tubular section 14. As illustrated in FIG. 11 in conjunction with FIG. 8, the staple cartridge support member 20 is formed of an outer housing of a suitable plastic material such as polycarbonate and is comprised of upper housing half section 112, a lower housing half section 114, and a cartridge support plate 166 attached by ultrasonic welding, adhesives, etc. The assembled staple cartridge support member 20 is attached to and integral with flange 16, which includes an indentation 116 at the proximal end having a "V-shaped" cross section and a similar indentation 118 also having a "V-shaped" cross section. Both indentations 116, 118 are adapted to respectively engageably receive the rounded distal ends of drive rods 102, 100, respectively, such that when the drive rods 100, 102 are respectively and alternatively moved in the proximal and distal directions as described hereinabove, one rod may advance distally to cause the lower housing 114 to rotate and the other rod withdraws to permit the pivotal motion of the lower housing 114 of the staple cartridge support member 20.

The staple cartridge support member 20 is adapted to be removably attached to a readily detachable staple cartridge 24 containing a plurality of surgical staples 120 which are fed individually to the staple cartridge support member 20 and which are particularly shaped to penetrate and to attach surgical mesh to body tissue. For particular details of the shape of the staples 120 constructed according to the invention, reference should be made to FIGS. 13–17.

In particular, lower housing half 114 includes stabilizing tabs 124*l*, 124*r* projecting distally from the distal end. During positioning of the staple cartridge support member 20 substantially adjacent body tissue or a mesh preparatory for staple insertion thereof, the stabilizing tabs 124*l*, 124*r* brace the staple cartridge support member 20 against firm or taut tissue, bone, or prosthetics underlying the body tissue/mesh targeted for staple insertion. For example, during hernia repair, the stapling of a mesh to the Ligament of Cooper requires stable positioning of the distal end of the apparatus despite the curved surface of the underlying pelvic bone. The stabilizing tabs 124*l*, 124*r* press against the mesh and underlying body tissue and/or bone to prevent the distal end from sliding as the lowermost staple 122 is advanced, inserted, and formed into the targeted body tissue/mesh. Tabs 124*l*, 124*r* also function as spacers so the staple is formed without contacting the Cooper's ligament.

The present invention utilizes a system of storage of the staples 120 similar to the system disclosed in copending commonly assigned application Ser. No. 07/950,425, filed Sep. 23, 1992. The staples 120 are positioned in adjacent stacked relation to form an angle with the longitudinal axis of the instrument of approximately 45° as shown in FIG. 8. One purpose of stacking the staples as shown is to provide greater visibility to the user by the fact that the outer surface of the staple cartridge 24 adjacent the stack of staples 120 forms a similar angle and provides visibility to the user at the distal end of the instrument 10. Angular stacking of the staples 120 as shown facilitates storage of a plurality of staples in a structure configured and dimensioned for use in stapling applications; e.g. for use through a trocar guide tube of diameter of about 12 mm for example. The stack of staples 120 as shown in FIG. 8 is positioned and retained in such position by a resilient spring member 126 having dual resilient legs and whose side profile is curved as shown in FIG. 11. In an alternative preferred embodiment, the staples are stacked substantially vertically rather than at an angle. This also facilitates visibility and storage.

The distal end of each leg engages the uppermost staple follower 128 in the form of a nylon insert having a general "H-shaped" configuration and dimensioned sufficient to cover the staples as best shown in FIG. 8. The nylon follower 128 is intended to transmit the downward force of the staple retainer spring 126 so as to distribute the force on the stack of staples 120 in a manner to facilitate a constant and uni-directional downward force on the lowermost staple which is positioned for advancement and deformation. It also functions to advance the stack of staples downwardly when the lowermost staple is fired. Anvil 130 is shown in FIG. 8 and includes upwardly extending legs 132, 134 which act as individual anvils at the distal end as shown in FIG. 8 for forming the staple therearound.

Thus, as seen in FIG. 8, the lowermost staple 122 is in a position for engagement by pusher plate 96 when the pusher assembly is advanced distally. The distal end of pusher plate 96 is shown clearly in FIGS. 13–15 and includes distally advancing lands 96r, 96l at the distal end to facilitate transmission of advancing force to the two rounded or arcuate bridge portions of the staple 122. This relative complementary configuration of the pusher plate 96 and the lowermost staple 122 facilitates efficient and uniform distribution of force to the staple when it is deformed about the anvil members as described below.

As illustrated in greater detail in FIGS. 13–15, the distal end of pusher plate 96 includes projections 96a, 96b forming a gap 96c therebetween. Projections 96a, 96b press against central bight portion 122c of staple 122 to counter the tendency of the central bight portion 122c to bend as the staple 122 is bent as shown in FIGS. 13–15. Thus, the central bight portion 122c is maintained in a substantially straight shape throughout forming of the staple 122.

The central gap 96c of pusher plate 96 serves to allow the central resilient member 136c of spring channel member 136 to spring upward in a position proximal to the central bight portion 122c, as described further below. Additionally, since the pusher plate 96 and staple 122 slide over the surface of anvil 130 to form the staple 122, as shown in FIGS. 13–15, the gap 96c of pusher plate 96 serves as a relief, allowing smooth distal and proximal motion of pusher plate 96 and staple 122 over anvil 130 without detracting from the structure of the pusher plate 96.

As shown in FIG. 8, a spring channel member 136 is positioned between the anvil 130 and the lower housing half 114. A proximally directed tab 138 extends from the distal end of anvil 130 having an aperture formed thereabove for receiving a central resilient member 136c of the spring channel member 136. The spring channel member 136 is positioned in a depressed cavity 140 at the distal end of the lower housing half 114, and the tab 138 of anvil 130 extends into a locating aperture 142 at the distal end of the lower housing half 114 for locating and positioning the anvil 130 substantially adjacent the lower housing half 114.

As illustrated in FIG. 9, the anvil 130 has legs 132, 134 extending upwardly and tab 138 extending downward from the distal end of the anvil 130. Proximal projections 144 extend downward for locating and positioning the anvil 130 substantially adjacent the lower housing half 114 by extending into apertures 146l, 146r at the proximal end of lower housing half 114 shown in FIG. 8. In conjunction with aperture 148 of anvil 130 for positioning projection 150 of the lower housing half 114, the projections 144 and tab 138 of anvil 130 cooperate with corresponding apertures 146l, 146r and aperture 142 to properly position anvil 130 between upper housing half 112 and lower housing half 114.

Referring to FIG. 9, anvil 130 also comprises projections 152, 154 extending downward from the anvil 130 to engage corresponding apertures 156, 158 of the spring channel member 136 as shown in FIG. 10. The anvil 130, including projections 152, 154, and the spring channel member 136 are made of stainless steel, so the apertures 156, 158 may also serve to position the anvil 130 substantially adjacent the spring channel member 136 for attachment thereof, such as by spot welding.

It will be appreciated that the staples 120 have a minute thickness and are pushed through a narrow channel of the distal end of the apparatus by pusher plate 96. The manufacturing of the spring channel member 136 from stainless steel with substantial precision provides a uniform channel for proper staple passage. The channel and pusher plate 96 allow for smooth operation of the instrument for inserting the staple 122 into tissue without difficulty.

It would therefore be advantageous to construct the stapler at the distal end in a manner to simplify the assembly of the components while providing a uniform channel passage for staples at all times. This is particularly applicable for a surgical stapler having components intended to determine a uniform channel for proper staple passage and which also prevent proximal movement of a staple during firing. The channel and pusher plate should allow for smooth operation of the instrument for inserting the staple into tissue without difficulty, while providing for smooth instrument operation.

It should be noted that in an alternative embodiment, the staple track can be formed by a unitary piece by molding the track in staple cartridge support member 20.

As illustrated in a top view in FIGS. 10 and 12 the spring channel member 136 may include a proximal portion 160 having apertures 156, 158 as described above. The spring channel member 136 also has side portions 162, 164 connected by traverse member 166 at the distal end of spring channel member 136. Each of the side portions 162, 164 forms an elongated slot for smooth passage therethrough of a surgical staple advanced distally over the flat upper surface of the anvil 130 by pusher plate 96 towards anvil legs 132, 134.

Referring once again to FIGS. 8 and 11, during assembly the spring channel member 136 and anvil 130 are positioned between cartridge support plate 166, upper housing half 112, and lower housing half 114. During the aforesaid positioning and attachment of the plastic components 112, 114, 166 by ultrasonic welding, adhesives, etc., the metallic spring channel member 136 and anvil 130 retain their shape so that the side portions 162, 164 of spring channel member 136 maintain a predetermined slot for smooth staple passage therethrough.

The spring channel member 136 includes central resilient member 136c and lateral resilient members 136l, 136r forming a "W" configuration at the distal end of the spring channel member 136. Anvil legs 132, 134 extend upward between the central resilient member 136c and lateral resilient members 136r, 136l, respectively, so a surgical staple 122 as shown in FIG. 11, for example, is biased upward by upwardly biased resilient members 136*l*, 136*r* as the staple 122 is advanced distally towards anvil legs 132, 134. Therefore, after the pusher plate 96 is withdrawn proximally, resilient members 136*l*, 136*r* raise the formed staple 122 as shown in FIG. 15 off anvil legs 132, 134 to disengage the formed staple 122 from the apparatus 10.

As the staple 122 is advanced distally by the pusher plate 96 against anvil legs 132, 134, the central resilient member 136*c* slidably engages the underside of staple 122 until the central bight portion 122*c* clears the central resilient member 136*c*. The central resilient member 136*c* then rises to a position proximal to the central bight portion 122*c*, and a central gap 96*c* in pusher plate 96 is adapted to receive the risen central resilient member 136*c* of the spring channel member 136.

In the event of a release in pressure from the trigger 28 causing pusher plate 96 to move proximally away from a distally advanced staple such as the staple 122 shown in FIG. 13, the risen central resilient member 136*c* prevents the advanced staple 122 from moving proximally, such that an advanced or partially advanced staple remains within the channel formed by the spring channel member and between the anvil legs 132, 134 and the central resilient member 136*c* until advancement and forming of the advanced staple by pusher plate 96 is resumed and completed.

As illustrated in FIG. 11, the staple cartridge support member 20 and the associated flange 16 are pivotally mounted at the distal end of tubular member 14 with the staple cartridge 24 removably mounted thereon. The structure of the staple cartridge support member 20 and staple cartridge 24 are described above and shown in FIG. 8 and are similar to staple cartridge support members and staple cartridges described in further detail in commonly assigned U.S. patent application Ser. No. 07/950,425, filed on Sep. 23, 1992, incorporated herein by reference.

In particular, the staple cartridge 24 has an upper housing half section 24*a* including a window 24*c* for receiving the proximal end 128*c* of follower 128 to indicate that the last surgical staple has been fired. The proximal end 128*b* of follower 128 in window 24*c* is identified phantom lines 128*c* in FIG. 11.

As shown in FIG. 12, the distal end of the apparatus 10 along lines 12—12 of FIG. 11 has cartridge support plate 166 with legs 166*l*, 166*r* positioned above the lower housing half section 114 with spring channel member 136 and side portions 162, 164 thereof therebetween. Side portions 136, 138 form the channel for passage of a staple therethrough, and resilient members 136*r*, 136*l*, 136*c* are positioned as described above. Anvil legs 132, 134 and projections 96*l*, 96*r* of pusher plate 96 are positioned to engage a staple in the channel of spring channel member 136, and stabilizer tabs 124*l*, 124*r* are positioned to stabilize the instrument 10 in use.

THE STAPLE CLOSING SYSTEM

Referring now to FIGS. 13–15 there is illustrated the sequential views of the staple advancing and closing system between the pre-fired and fired condition of the staple. In particular, the staple and pusher mechanism are shown in FIG. 13 in the pre-fired condition, the staple 122 is shown in an intermediate formation condition in FIG. 14, and the staple 122 shown in FIG. 15 is in the final formed condition in which the staple 122 is embedded within the body tissue.

In FIG. 13, the staple pusher assembly is positioned proximal of the lowermost staple 122 and pusher plate 96 is correspondingly positioned proximal of the lowermost staple 122. In FIGS. 14–15, the pusher plate 96 has been partially advanced and fully advanced, respectively, in the distal direction. The lowermost staple 122 has been advanced distally of the stack of staples 120 in a manner such that the pusher plate 96 has now replaced lowermost staple 122 thereby preserving the integrity and position of the stack of staples 120. The preservation of the stack of staples 120 is provided by the fact that the thickness of the staple pusher plate 96 is either identical to or slightly less than the thickness of the staples for the pusher plate 96 to engage only one staple at a time.

Referring further to FIGS. 14–15 the pusher plate 96 has now advanced distally sufficient to cause the staple to penetrate the body tissue and/or a surgical mesh between the staple 122 and the body tissue. As shown in FIGS. 13–15, it can be seen that anvil legs 132, 134 have arcuate convex surfaces 132*a*, 134*a*, respectively on their proximal sides as shown in FIGS. 13–15, and are positioned for engagement by the correspondingly located arcuate concave distal surfaces of bridge portions 122*br* and 122*bl* of the backspan of the staple 122 such that engagement of the staple 122 by the distally extending legs 96*r* and 96*l* of pusher plate 96, with the arcuate end corner portions of the staple as shown, causes the staple to deform in a predetermined manner as described below. In the preferred embodiment, the proximal portion of each of the anvil legs 132, 134 is rounded to insure that the bridge portions 122*br*, 122*bl* are formed by curving therearound to bend the staple leg members 122*l*, 122*r* inward as shown in FIG. 15.

In FIG. 15 the staple 122 is now shown in the deformed condition about the anvil legs 132, 134 and the straight portions of the back rib of the staple 122 are still in engagement with the anvils legs 132, 134. In FIG. 15, the staple 122 has penetrated into the body tissue and has been deformed and the staple deformation is completed. The inwardly, projecting central portion or bight 122*c* of staple 122 is shown in cooperation with the staple legs as shown in FIG. 15. However, in FIG. 15 release of the staple 122 from the anvil members 132, 134 has not yet been completed.

Release of the staple from the anvil members 132, 134 is readily accomplished by the resilient members 136*l*, 136*r* acting as ejector springs of spring channel member 136. When the pusher plate 96 is in the position shown in FIGS. 14–15, the resilient members 136*l*, 136*r* of spring channel member 136 are retained in a downward position by lands 96*l*, 96*r* of the pusher plate 96. However, when the pusher plate 96 is moved in a proximal position such as shown in FIG. 13, the absence of the pusher plate 96 permits resilient members 136*l*, 136*r* to resiliently deflect upwardly to their natural configuration thereby creating a vertical separation between the anvil legs 132, 134 and the deformed staple, thus releasing the deformed staple from the anvil members. Continued proximal movement of the pusher plate 96 causes withdrawal of the pusher plate to a position entirely proximal of the stack of staples 120 as shown in FIG. 11, causing the stack of staples 120 to move downwardly due to the downward force of resilient staple retainer spring 126 to advance the lowermost staple to the firing position.

Once the staple 122 is applied to the body tissue, the distal end of staple cartridge 24 is withdrawn from the staple target area and preparation is made for application of the next staple. Thereafter, the apparatus may be repositioned to apply another staple, or even an array of staples.

It should be noted that the instrument can be used for repair of body tissue utilizing a surgical mesh in a manner to either reinforce a surgical repair or to encourage tissue growth. Such mesh materials are typically disclosed in U.S. Pat. Nos. 4,838,884, 4,665,221, 4,452,245, and 4,347,847. It is noted that the staple 122 constructed according to the invention provides for attachment of such mesh material to body tissue according to any number of techniques which may readily come to the mind of those skilled in the art. In fact, in some instances the mesh may be formed as a plug for insertion into a surgical opening and then stapled. Moreover, the apparatus and staple of the present invention may be applied to attach other objects to body tissue as may come to the mind of those skilled in the art. The staple can also be applied to attach portions of body tissue directly.

THE STAPLE

Referring now to FIGS. 13–17, there is illustrated the staple 122 constructed according to the invention. The staple 122 is particularly shaped as shown, and is preferably formed of a length of wire of titanium. FIG. 16 illustrates a perspective view of the staple 122. The staple 122 preferably has a rectangular cross-section as shown in FIG. 17. Typically, the wire is about 0.51 mm in width (dimension W in FIGS. 13 and 16–17) and 0.38 mm in thickness (dimension T in FIGS. 16–17). The initial width of the staple before closure (dimension A in FIGS. 13 and 17) is about 8.64 mm and the thickness dimension between the back rib and legs after closure (dimension B in FIG. 15) is about 2.5 mm. The staple 122 has a central bight portion 122c and wire leg members 122l, 122r extending generally perpendicular to the central portion as shown. Each leg member 122r, 122l is connected to the central portion 122c by a bridge portion 122bl, 122br having an arcuate corner portion as shown. Each leg member has a sharp tip for penetrating mesh and body tissue. Right leg member 122r further possesses a tapered surface 122tr at the tip which is opposite the position of the tapered surface 122tl at the tip of the other leg member 122l.

When the lowermost staple 122 shown in FIG. 11 is advanced toward dual spaced anvils 132, 134 as shown in FIGS. 13–15 for example, staple pusher plate 96 as shown engages the arcuate portions of the bridge portions 122br and 122bl, and the legs of the staples are made to fold inwardly toward each other as shown for example in FIG. 15, with one leg crossing over the other. The cross-over configuration is automatically assumed by the legs because of the presence of tapered surfaces 122tr and 122tl which act as camming surfaces tending to bias each leg away from the other thereby tending to cross the legs in the manner shown. This structure also prevents interference of the legs when folded toward each other.

Thus, it can be seen that the particular shape of the staple as shown in FIGS. 13–17 promotes a folding pattern for the legs which achieves the configuration shown in the bent staple 122 of FIG. 15. This staple shape combines with the arrangement of the anvils and the particularly configured pusher plate 96 to cause the staple to pierce mesh and body tissue up to a predetermined extent. At this point, continued application of force to the staple causes the staple legs to fold upon themselves as shown in the drawings while encompassing a sufficient portion of the mesh to attach the mesh to the body tissue. Thus the staple pierces folds and grips in substantially a single movement.

ALTERNATIVE EMBODIMENTS

As noted above, in a preferred alternative embodiment, first star wheel 30 is eliminated and the relief 46 in handle 26 is also eliminated. Star wheel 32 is arranged to provide several functions, as first noted. The first function is to articulate the staple cartridge 24 and cartridge support 20 from 0° to a predetermined angle, (i.e. 45° in the preferred embodiment disclosed herein) by longitudinal proximal movement thereof. The second function is to return the cartridge to 0° by distal movement thereof. The third function is to rotate the entire tubular section 14 and the cartridge 24 by direct connection therebetween as described hereinabove so that the cartridge may be made to sweep a conical path when it is articulated to 45° and the tubular section 14 is rotated up to a full 360°.

In another alternative embodiment, as shown in FIGS. 18–19, the apparatus 210 may be a non-articulating surgical stapler including handle 212, grip 226, trigger 228, trigger stop device 274, and non-articulating elongated section 214 having a longitudinal axis and a distal end 214d adapted to receive detachable staple cartridge 24. In this embodiment, first star wheel 230 positioned in relief 212a of handle 212 is appropriately connected to the staple pusher system to rotate the non-articulating tubular section 214 about the longitudinal axis. Any number of known connection techniques similar to those described previously may be used. The alternative non-articulating surgical stapler 210 may incorporate the various features of the articulating stapler 10 as described above for FIGS. 1–15, such as stabilizing tab 224l and a spring channel member as in the previous embodiment.

Combinations of features of the present embodiment may be combined with features described in connection with the previous embodiment as may become apparent to persons skilled in the art.

What is claimed is:

1. Apparatus for applying at least one surgical fastener to body tissue, which comprises:
   a) a frame;
   b) a tubular member connected to said frame and extending distally therefrom, said tubular member having a generally longitudinal axis, a proximal end portion, and a distal end portion;
   c) at least one surgical fastener supported by said tubular member;
   d) means for advancing said at least one surgical fastener distally for positioning adjacent the body tissue; and
   e) articulating means for pivoting said distal end portion to predetermined angles with respect to said generally longitudinal axis, said articulating means including:
      i) rotatable means rotatable about an axis generally transverse to said longitudinal axis and engageable with at least two pushrods movable in proximal and distal directions for engaging and pivoting the distal end portion, said rotatable means defining a generally V-shaped aperture; and
      ii) control means which includes a generally elongated member extending generally transverse to said longitudinal axis and received by said generally V-shaped aperture for operative engagement therewith whereby movement of said control means proximally and distally causes rotation of said rotatable means about said generally transverse axis to thereby move said push rods for pivoting the distal end portion.

2. Apparatus according to claim 1 wherein said at least one fastener is supported by fastener storing means, said fastener storing means being removably supported by said tubular member.

3. Apparatus according to claim 1 wherein said control means comprises a collar positioned about a proximal portion of said tubular member for moving longitudinally in proximal and distal directions to control the pivoting of said distal end portion.

4. Apparatus according to claim 3 wherein said collar is movable to at least one stable position which corresponds to a predetermined pivot angle of said distal end portion relative to said longitudinal axis.

5. Apparatus according to claim 1, further comprising means for closing said at least one surgical fastener.

6. Apparatus according to claim 5 wherein said fastener advancing means includes a spring channel member defining a channel dimensioned and configured to allow at least one surgical fastener to pass therethrough.

7. Apparatus according to claim 6 wherein said spring channel member comprises resilient means for moving a closed surgical fastener from said fastener closing means.

8. Apparatus according to claim 7 wherein said spring channel member includes a projection for preventing at least one surgical fastener from moving in a proximal direction.

9. Apparatus according to claim 5 wherein at least one fastener is positioned in a cartridge, said cartridge being retained in a cartridge support member, and said fastener closing means comprises an anvil having at least two projections and said cartridge support member includes an aperture for correspondingly locating said projections of said fastener closing means to position said fastener closing means substantially adjacent said cartridge support member.

10. Apparatus according to claim 9 wherein said anvil comprises at least two upstanding staple closing anvil members each having a proximal curved surface corresponding to similar distal curved surfaces on the backspan of a surgical fastener.

11. Apparatus according to claim 9 wherein said aperture and said projections are located at a distal portion of said cartridge support and closing means, respectively.

12. Apparatus according to claim 9 wherein said aperture and said projections are located at a proximal portion of said cartridge support and closing means, respectively.

13. Apparatus according to claim 9 wherein said cartridge support member includes a projection for positioning a portion of said anvil substantially adjacent said cartridge support.

14. Apparatus according to claim 13 wherein said anvil includes an aperture for correspondingly locating the projection of said cartridge support to position said closing means substantially adjacent said cartridge support.

15. Apparatus according to claim 1 wherein said at least one fastener is positioned in a cartridge and said control means comprises a collar member mechanically connected to pivot said cartridge and adapted to retain said cartridge at a 0° angle relative to said longitudinal axis when said collar member is located at a predetermined distalmost position.

16. Apparatus according to claim 15 wherein said collar member is movable to at least a second position proximal of said first position to effect pivotal movement of said cartridge to an angle of about 45° relative to said longitudinal axis of said tubular member.

17. Apparatus according to claim 15 wherein said rotatable means comprises a disc-like member for mechanically connecting said collar member and said cartridge in a camming relationship.

18. Apparatus according to claim 17 wherein said disc-like member comprises means for setting said cartridge at a predetermined angle relative to said longitudinal axis of said tubular member.

19. Apparatus according to claim 17 further comprising at least one rod mechanically connecting said cartridge with a camming surface of a detent of said disc-like member to longitudinally move said rod for pivoting said cartridge.

20. Apparatus according to claim 15 wherein said tubular member comprises a cartridge support member for releasably retaining said cartridge.

21. Apparatus for applying at least one surgical staple to body tissue, which comprises:
 a) a frame;
 b) a tubular member connected to said frame and extending distally therefrom, said tubular member defining a longitudinal axis;
 c) at least one surgical staple;
 d) staple advancing mechanism operable for individually advancing said at least one surgical staple distally at least when said cartridge is generally in alignment with said longitudinal axis for positioning adjacent the body tissue;
 e) an anvil for closing the at least one surgical staple;
 f) a rotatable member rotatable about an axis generally transverse to said longitudinal axis and engageable with at least two pushrods and cooperative with said tubular member and having at least one generally V-shaped slot; and
 g) a control member directly engageable with said rotatable member and manually movable longitudinally in proximal and distal directions, said control member including a generally elongated member extending generally traverse to said longitudinal axis and received by said generally V-shaped slot for engagement therewith, whereby proximal and distal movement of said control member causes rotation of said rotatable member about said generally transverse axis to thereby move said push rods for pivoting the distal end portion.

22. Apparatus according to claim 21 wherein said a plurality of surgical staples are stored in a cartridge, said cartridge being connected to support means pivotally attached at the distal end portion of said tubular member.

23. Apparatus according to claim 22 wherein said control member pivots said cartridge from a proximal location.

24. Apparatus for application of a surgical staple to body tissue, which comprises:
 a) a handle;
 b) a tubular member extending distally from said handle;
 c) a cartridge for storing at least one surgical staple;
 d) a pusher for advancing said at least one surgical staple distally for application to body tissue;
 e) an anvil for closing said at least one surgical staple; and
 f) a rotatable disc-like member positioned for rotation and selective engagement with at least two pushrods adapted for articulating a distal portion of said tubular member to selected angles relative to a longitudinal axis of said generally tubular member, said rotatable disc-like member defining at least one generally V-shaped slot; and
 g) a control member extending about a proximal portion of said tubuler member and movable in proximal and distal directions and having a generally elongated member extending generally transverse to said longitudinal axis, said generally elongated member being directly engagable with said generally V-shaped slot of said rotatable disc-like member to cause rotation of said disc-like member when said control member is moved proximally and distally, whereby said pushrods are engaged and moved so as to effect activation of said distal portion.

25. Apparatus according to claim 24 wherein said pusher includes at least two distal projections for applying pressure to a backspan of said at least one surgical staple to close said staple by said anvil in a manner to prevent the backspan from bending.

26. Apparatus according to claim 25 wherein said pusher includes a gap formed between said at least two distal projections for providing relief to said pusher to slide smoothly over said anvil.

27. Apparatus according to claim 24 wherein said anvil includes at least two upstanding legs for closing said at least one surgical staple while applying same to body tissue.

28. Apparatus according to claim 27 wherein said legs each include a rounded portion for forming said at least one surgical staple therearound to close said at least one surgical staple.

29. Apparatus according to claim 28 further comprising a spring channel for passage of said at least one surgical staple and having an upwardly biased resilient member for lifting each said staple upwardly from said anvil after formation therearound.

30. Apparatus according to claim 24 wherein said cartridge is supported on a pivotally mounted cartridge support member having at least two distally extending tabs engaging body tissue for stabilizing said cartridge relative to the body tissue during application of said staples.

* * * * *